(12) United States Patent
Nicholas

(10) Patent No.: US 11,350,942 B2
(45) Date of Patent: Jun. 7, 2022

(54) FLEXIBLE SURGICAL STAPLER

(71) Applicant: Covidien LP, Mansfield, MA (US)

(72) Inventor: David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 10 days.

(21) Appl. No.: 17/107,518

(22) Filed: Nov. 30, 2020

(65) Prior Publication Data

US 2021/0077113 A1 Mar. 18, 2021

Related U.S. Application Data

(63) Continuation of application No. 15/966,130, filed on Apr. 30, 2018, now Pat. No. 10,849,628.

(Continued)

(51) Int. Cl.
*A61B 17/115* (2006.01)
*A61B 17/072* (2006.01)
(Continued)

(52) U.S. Cl.
CPC .... *A61B 17/1155* (2013.01); *A61B 17/07207* (2013.01); *A61B 2017/0046* (2013.01);
(Continued)

(58) Field of Classification Search
CPC . A61B 17/115; A61B 17/1155; A61B 17/068; A61B 2017/00367; A61B 2017/2903; A61B 2017/2905; A61B 17/072; A61B 34/35; A61B 34/70; A61B 2017/00398; A61B 2017/00477; A61B 2017/0046
See application file for complete search history.

(56) References Cited

U.S. PATENT DOCUMENTS 9,055,943 B2   6/2015 Zemlok et al.
9,078,687 B2 * 7/2015 Rohaninejad ...... A61B 17/2833
(Continued)

FOREIGN PATENT DOCUMENTS

EP   2823771 A1   1/2015
EP   3078335 A1   10/2016
EP   3153113 A1   4/2017

OTHER PUBLICATIONS

European Search Report dated Feb. 27, 2019, issued in EP Appln. No. 18176937.

*Primary Examiner* — Andrew M Tecco
*Assistant Examiner* — Jacob A Smith
(74) *Attorney, Agent, or Firm* — Carter, DeLuca & Farrell LLP

(57) ABSTRACT

A flexible surgical stapler includes an adapter having a coupling assembly configured for securing the adapter assembly to a handle assembly, an elongate body extending from the coupling assembly, a first drive assembly extending through the elongate body, and a loading unit secured to a distal portion of the elongate body. The loading unit includes a firing assembly operably connected to the first drive assembly. The firing assembly includes a cycloid gear assembly for increasing an input torque from the first drive assembly to actuate the firing assembly. The flexible surgical stapler may include an introducer assembly to facilitate introduction of a stapling portion of the surgical stapler into a body cavity of a patient.

11 Claims, 20 Drawing Sheets

Related U.S. Application Data

(60) Provisional application No. 62/518,395, filed on Jun. 12, 2017.

(51) Int. Cl.
*A61B 17/29* (2006.01)
*F16H 1/32* (2006.01)
*A61B 17/00* (2006.01)

(52) U.S. Cl.
CPC ............ *A61B 2017/00292* (2013.01); *A61B 2017/00336* (2013.01); *A61B 2017/00367* (2013.01); *A61B 2017/00738* (2013.01); *A61B 2017/07221* (2013.01); *A61B 2017/07257* (2013.01); *A61B 2017/07271* (2013.01); *A61B 2017/2903* (2013.01); *A61B 2017/2905* (2013.01); *F16H 1/32* (2013.01)

(56) References Cited

U.S. PATENT DOCUMENTS

| | | | |
|---|---|---|---|
| 9,168,042 | B2 | 10/2015 | Milliman |
| RE46,135 | E | 9/2016 | Hibner |
| 9,554,802 | B2 | 1/2017 | Williams et al. |
| 10,849,628 | B2 | 12/2020 | Nicholas |
| 2004/0111081 | A1 | 6/2004 | Whitman et al. |
| 2005/0187576 | A1* | 8/2005 | Whitman ............ A61B 17/068 606/219 |
| 2006/0151568 | A1* | 7/2006 | Weller ............... A61B 17/0218 227/175.1 |
| 2007/0055219 | A1 | 3/2007 | Whitman et al. |
| 2008/0140118 | A1* | 6/2008 | Martinek ........... A61B 17/0625 606/232 |
| 2008/0188891 | A1* | 8/2008 | Frank ................... A61B 17/062 606/208 |
| 2009/0012538 | A1* | 1/2009 | Saliman ........... A61B 17/0491 606/145 |
| 2009/0101692 | A1 | 4/2009 | Whitman et al. |
| 2009/0182193 | A1 | 7/2009 | Whitman et al. |
| 2011/0257636 | A1 | 10/2011 | Whitman et al. |
| 2014/0012237 | A1 | 1/2014 | Pribanic et al. |
| 2014/0131418 | A1* | 5/2014 | Kostrzewski ........ A61B 17/068 227/176.1 |
| 2014/0243599 | A1* | 8/2014 | Farin ...................... A61B 17/34 600/114 |
| 2014/0246471 | A1 | 9/2014 | Jaworek et al. |
| 2015/0014392 | A1 | 1/2015 | Williams et al. |
| 2015/0157321 | A1 | 6/2015 | Zergiebel et al. |
| 2015/0374366 | A1 | 12/2015 | Zergiebel et al. |
| 2015/0374370 | A1 | 12/2015 | Zergiebel et al. |
| 2016/0106406 | A1 | 4/2016 | Cabrera |
| 2016/0270780 | A1 | 9/2016 | Hall |
| 2016/0310134 | A1 | 10/2016 | Contini et al. |
| 2016/0374669 | A1 | 12/2016 | Overmyer |
| 2017/0007254 | A1 | 1/2017 | Jaworek et al. |

\* cited by examiner

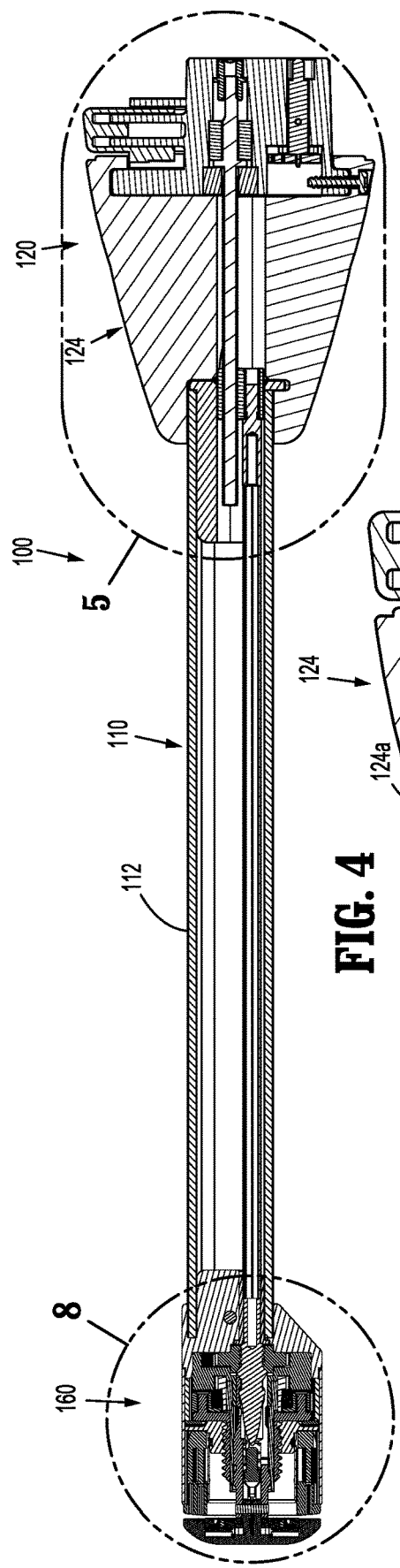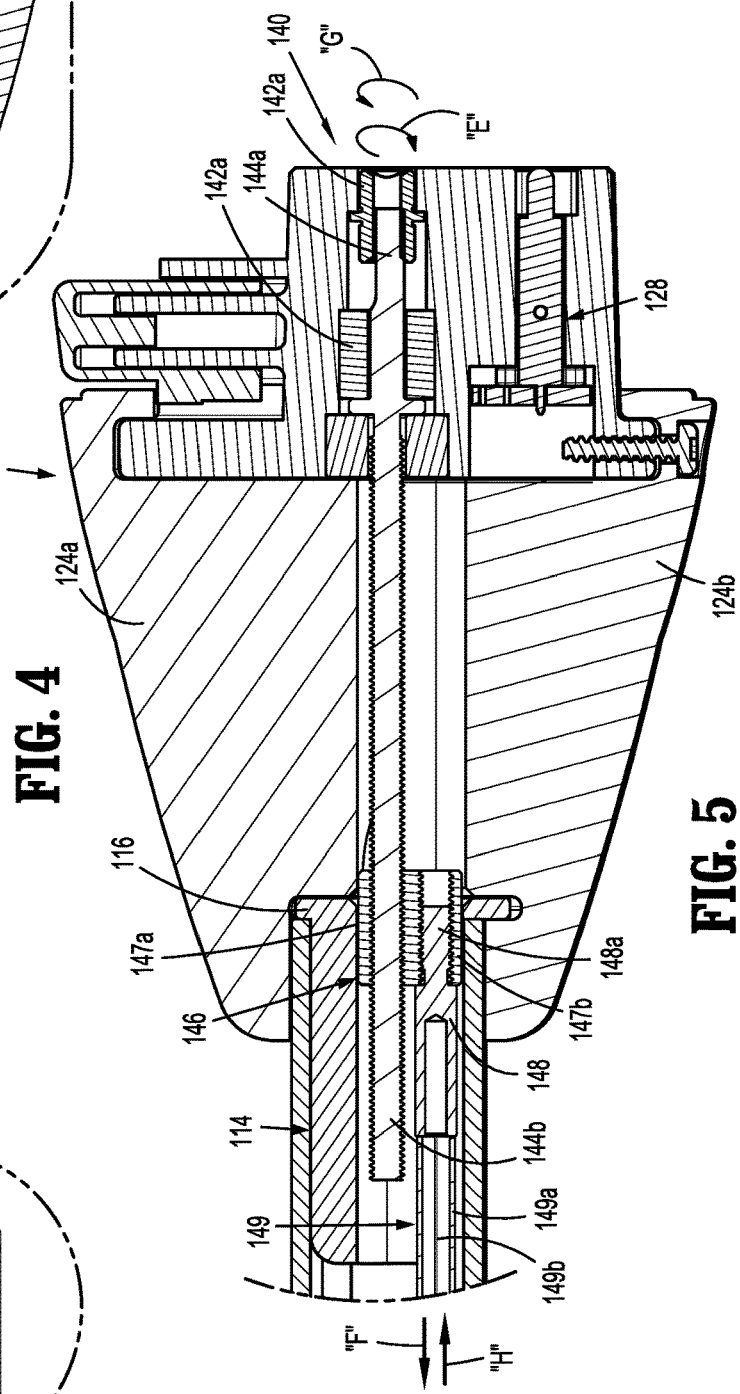
FIG. 4
FIG. 5

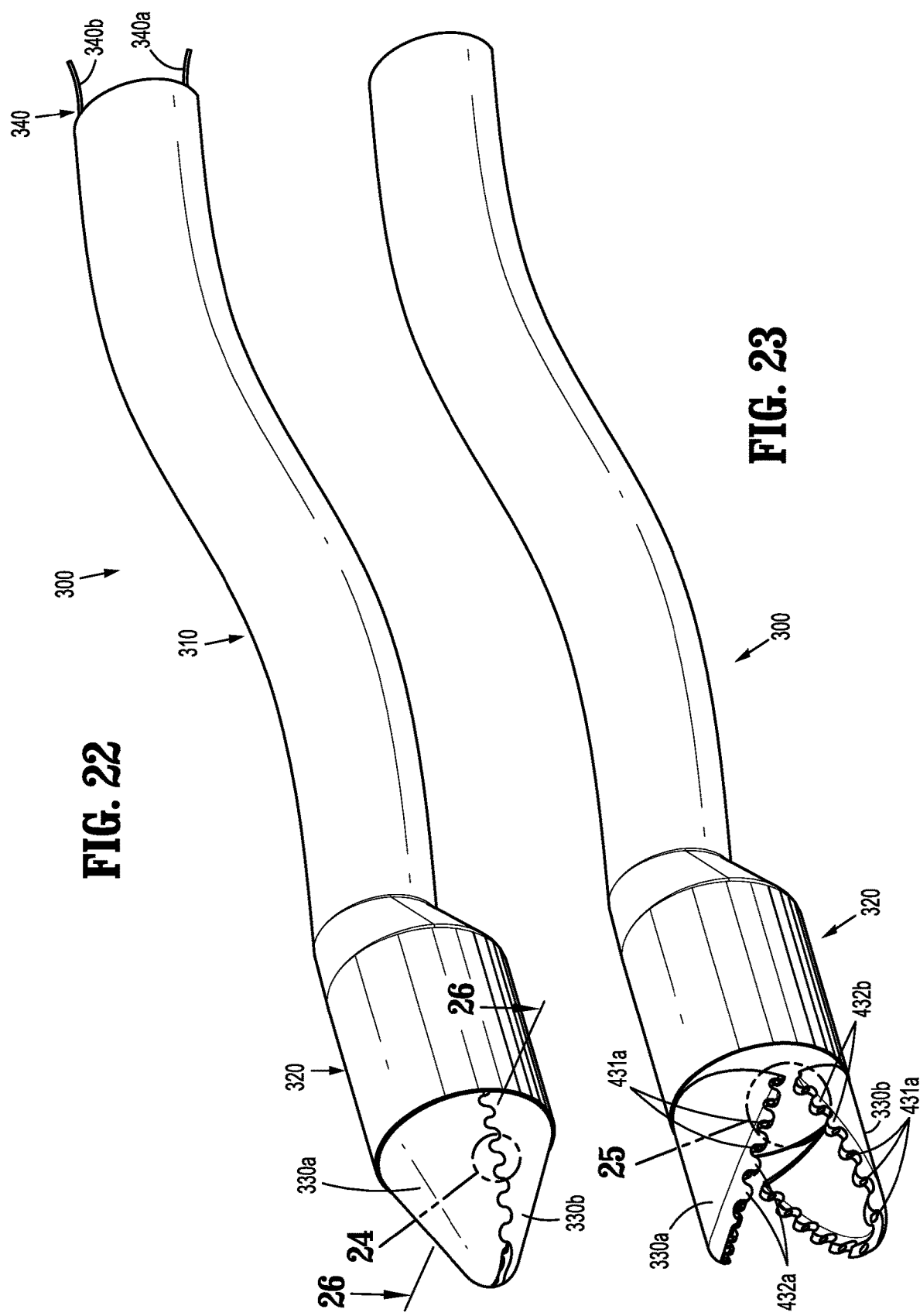

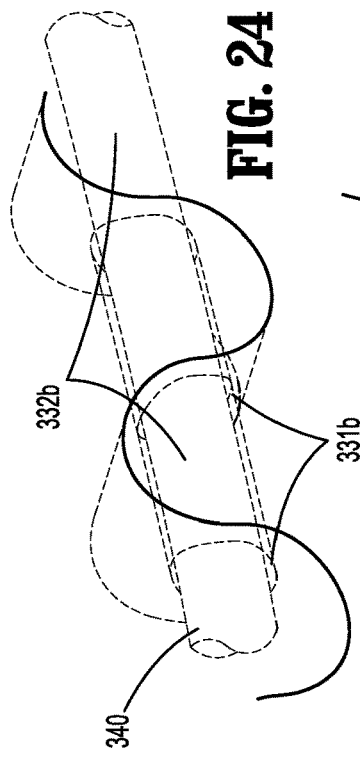
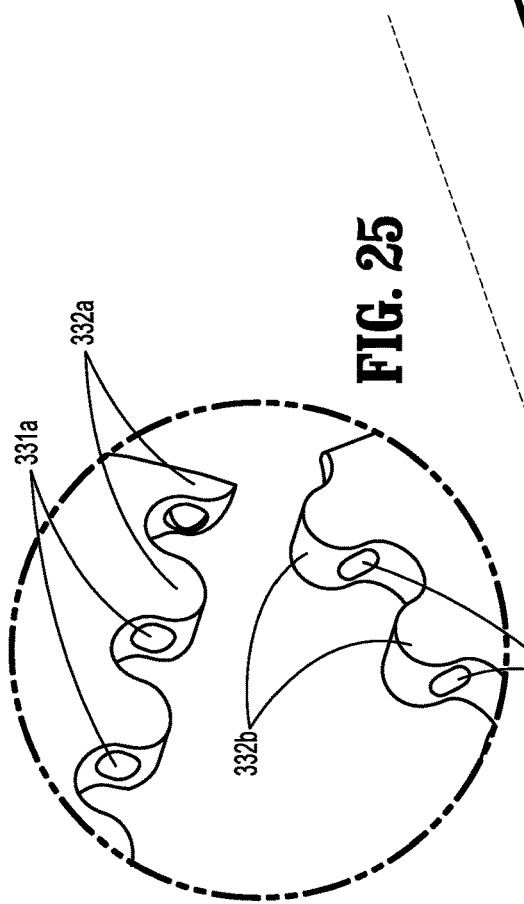
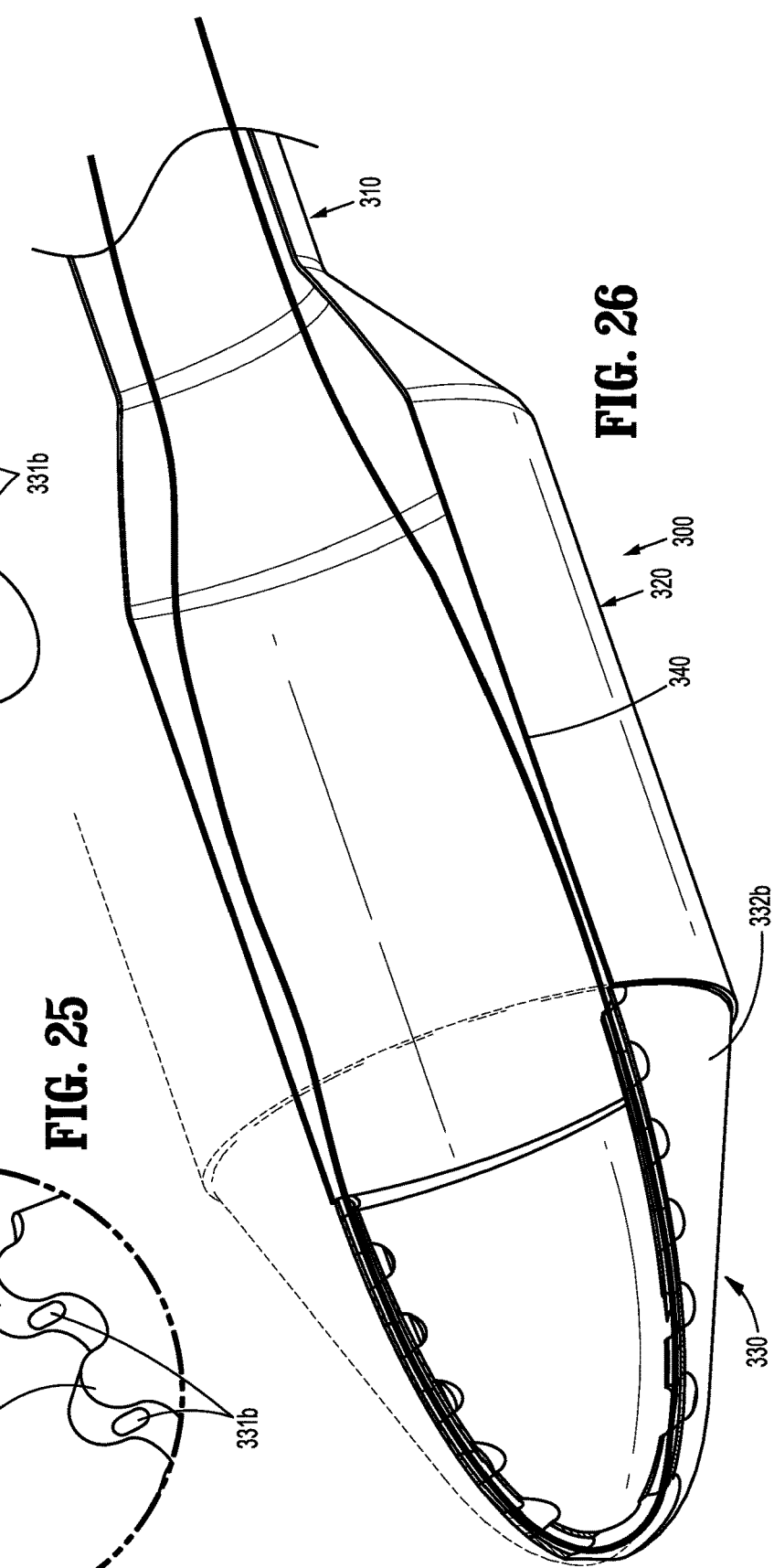

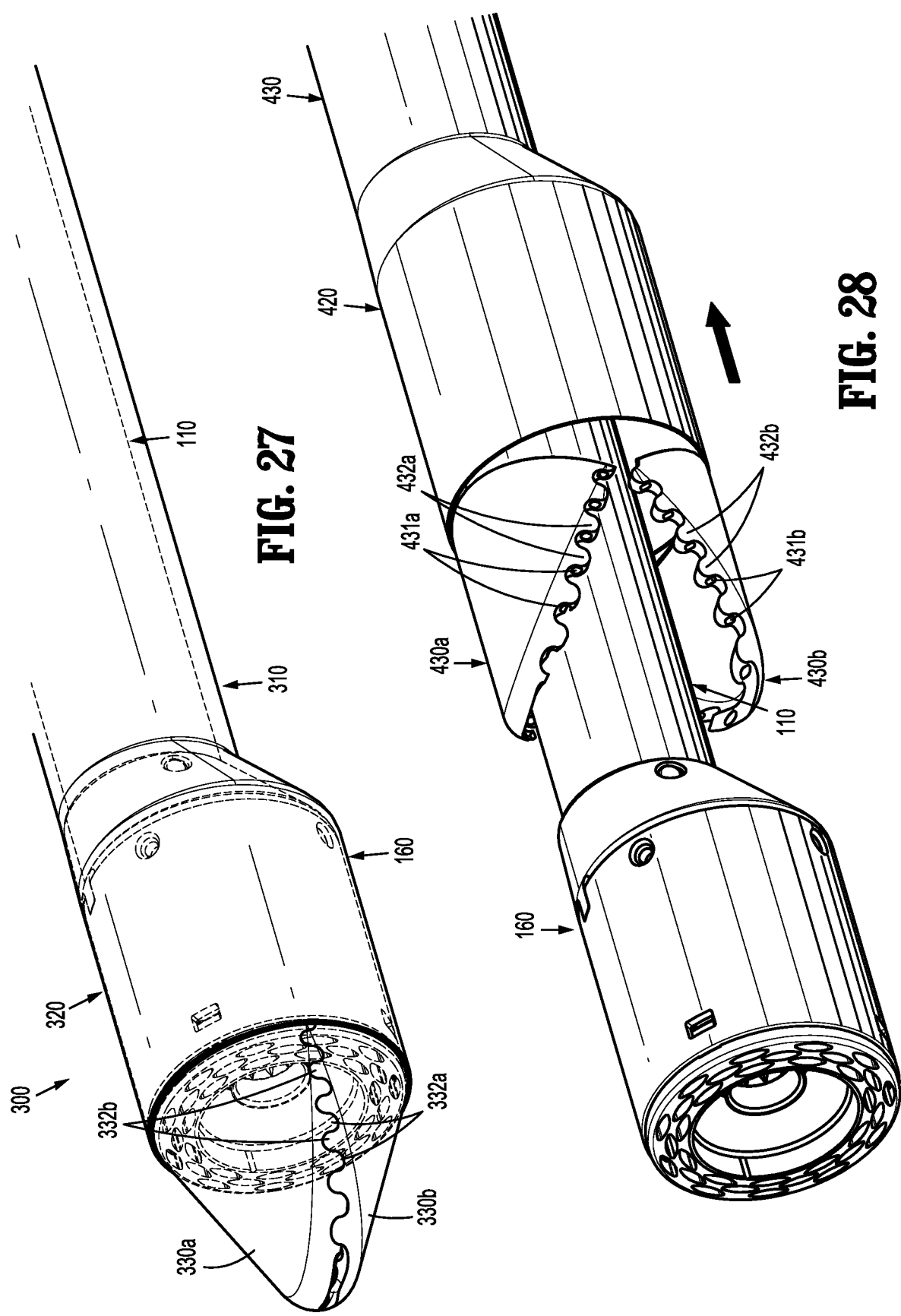

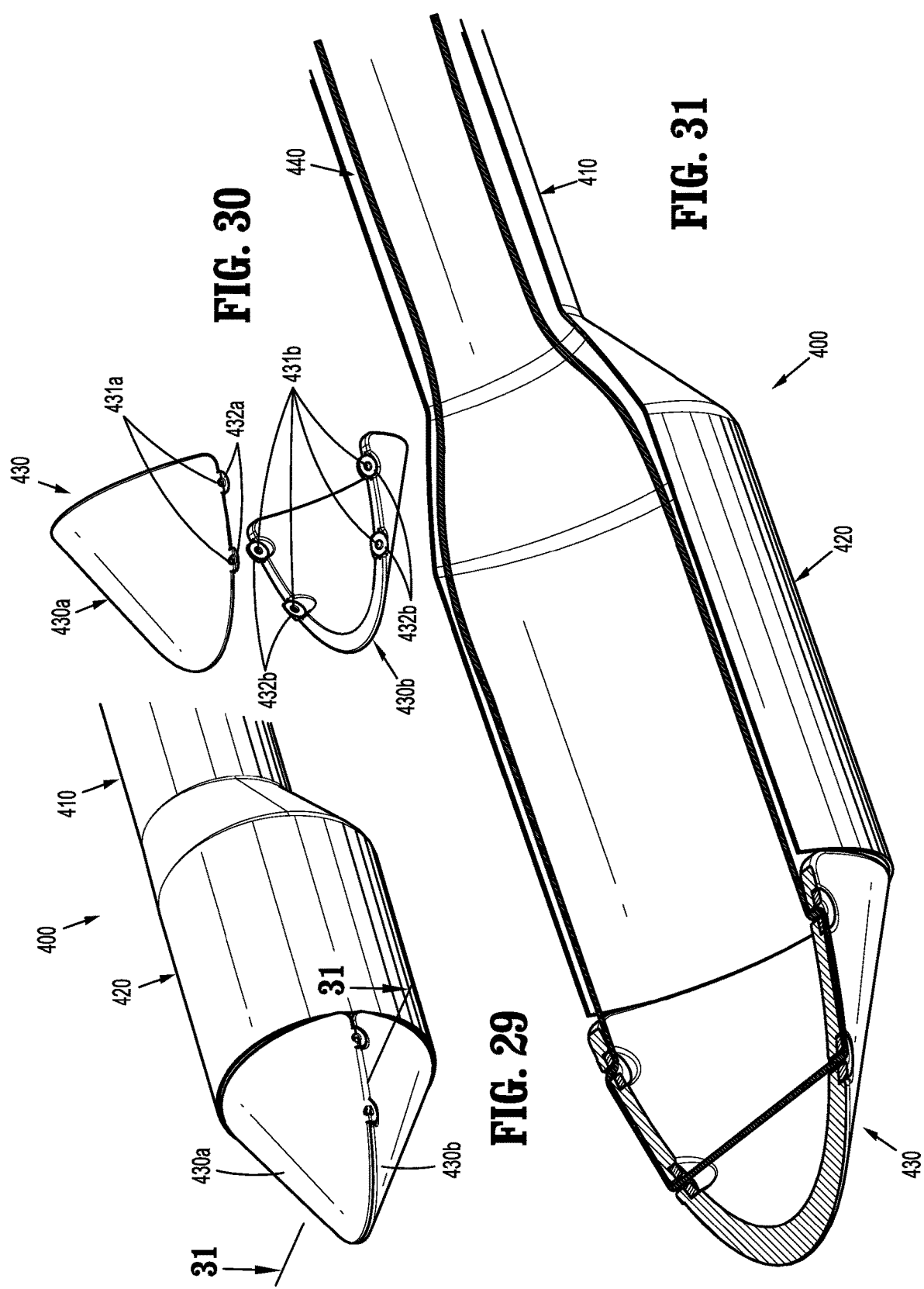

FLEXIBLE SURGICAL STAPLER

CROSS-REFERENCE TO RELATED APPLICATIONS

The present application is a continuation of U.S. patent application Ser. No. 15/966,130, filed Apr. 30, 2018, the entire contents of which are incorporated herein by reference.

BACKGROUND

Technical Field

The present disclosure relates to surgical stapler devices. More particularly, the present disclosure relates to flexible circular staplers.

Background of Related Art

Surgical staplers for performing surgical procedures within a body cavity of a patient are known. Typically, a stapling assembly is secured to a distal portion of an elongate shaft of the surgical staplers to facilitate introduction of the stapling assembly within the body cavity. Generally, the elongate shafts of the surgical staplers are rigid.

To facilitate introduction of a stapling assembly of a surgical stapler along a tortuous path, it would be beneficial to have a surgical stapler having a flexible elongate shaft.

SUMMARY

An adapter with a flexible elongate body is provided. The adapter includes a coupling assembly configured for securing the adapter assembly to a handle assembly, an elongate body extending from the coupling assembly, a first drive assembly extending through the elongate body, and a loading unit secured to a distal portion of the elongate body. The loading unit includes a firing assembly operably connected to the first drive assembly. The firing assembly includes a cycloid gear assembly for increasing an input torque from the first drive assembly to actuate the firing assembly.

In embodiments, the adapter assembly further includes a second drive assembly extending through the elongate body. The second drive assembly may be configured to effect gross movement of a trocar member through the loading unit.

The adapter assembly may further include a third drive assembly extending through the elongate body. The third drive assembly may be configured to effect fine movement of a trocar member within the loading unit.

Embodiments of the loading unit of the adapter assembly may include an approximation assembly. Each of the second and third drive assemblies may be operably connected to the approximation assembly. The second drive assembly may include a drive screw and a push/pull cable movably secured to the drive screw by a threaded nut. Rotation of the drive screw may cause longitudinal movement of the push/pull cable. The trocar member of the adapter assembly may be disposed on a distal portion of the push/pull cable.

The first and third drive assemblies may each include a flexible rotatable drive shaft and an input gear disposed on a distal portion of each of the flexible rotatable drive shafts. The input gear of the first drive assembly may rotate an internally threaded gear to finely move the trocar member relative to the loading unit. The trocar member may include a threaded intermediate portion configured to engage the internally threaded gear. Rotation of the internally threaded gear may cause longitudinal movement of the trocar member.

In embodiments, the firing assembly may further include a spider gear having an external thread, and a jack nut having an internal thread. The external thread of the spider gear may engage the internal thread of the jack nut such that rotation of the spider gear causes longitudinal movement of the jack nut. The firing assembly may also include a pusher assembly secured to the jack nut for ejecting staples from the loading unit.

A surgical stapling instrument with a flexible body portion is provided. The surgical stapling instrument includes a handle assembly, an adapter assembly extending from the handle assembly, and a loading unit disposed on a distal end of the adapter assembly. The loading unit includes a firing assembly including a cycloid gear assembly for increasing an input torque from the handle assembly to actuate the firing assembly.

Also provided is an introducer assembly for facilitating introduction of a stapling assembly into a body cavity of a patient. The introducer assembly includes a sleeve body, a sleeve housing secured to a distal end of the sleeve body, and first and second jaw members secured to a distal end of the sleeve housing and moveable between an open condition and a closed condition. Each of the first and second jaw members includes a plurality of openings configured to receive a suture when the first and second jaw members are in the closed condition to maintain the first and second jaws in the closed position.

In embodiments, each of the first and second jaw members includes a plurality of interlocking teeth. The each tooth of the plurality of interlocking teeth defines an opening of the plurality of openings. In other embodiments, each of the first and second jaw members includes a plurality of overlapping tabs. Each tab of the plurality of tabs defines an opening of the plurality of openings.

A surgical stapling kit is also provided. The kit includes a handle assembly, an adapter assembly, an anvil assembly, and an introducer member. The adapter assembly includes a loading unit disposed on a distal end thereof. The loading unit includes a firing assembly including a cycloid gear assembly for increasing an input torque from the handle assembly to actuate the firing assembly.

BRIEF DESCRIPTION OF THE DRAWINGS

The accompanying drawings, which are incorporated in and constitute a part of this specification, illustrate embodiments of the present surgical staplers and, together with a general description of the disclosure given above, and the detailed description of the embodiment(s) given below, serve to explain the principles of the disclosure, wherein:

FIG. 4 is a side cross-sectional view of the adapter assembly shown in FIG. 2;

FIG. 5 is an enlarged view of the indicated area of detail in FIG. 4;

FIG. 22 is a side perspective view of an introducer according to an embodiment of the present disclosure, with a jaw assembly in a closed condition;

FIG. 23 is a side perspective view of the introducer shown in FIG. 22, with the jaw assembly in an open position;

FIG. 24 is an enlarged view of the indicated area of detail shown in FIG. 22;

FIG. 25 is an enlarged view of the indicated area of detail shown in FIG. 23;

FIG. 26 is a top cross-sectional view taken along line 26-26 shown in FIG. 22;

FIG. 27 is a perspective view of the introducer shown in FIG. 22 received about a distal end of the adapter assembly shown in FIG. 2, with the jaw assembly in the closed condition;

FIG. 28 is a perspective view of the introducer shown in FIG. 22 received about the distal end of the adapter assembly shown in FIG. 2, with the jaw assembly in the closed condition;

FIG. 29 is a side perspective view of an introducer according to another embodiment of the present disclosure;

FIG. 30 is a perspective view of the jaw assembly of the introducer shown in FIG. 29, with parts separated; and FIG. 31 is a top cross-sectional view taken along line 31-31 shown in FIG. 29.

DETAILED DESCRIPTION

Figure 1:
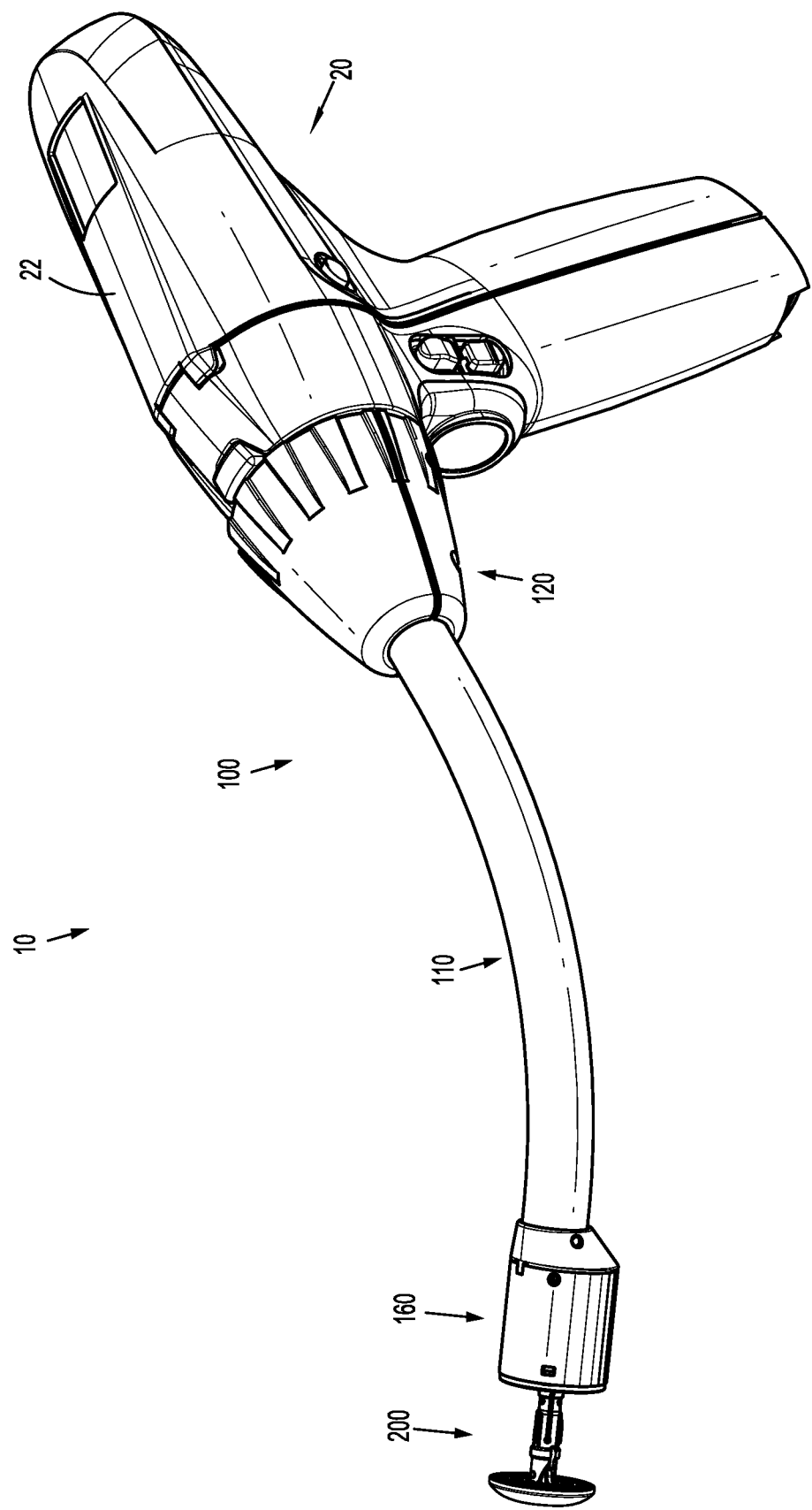
FIG. 1 is a side perspective view of a surgical stapling device according to an embodiment of the present disclosure, the surgical stapling device including a handle assembly, an adapter assembly having a loading unit, and an anvil assembly.

Embodiments of the present surgical staplers are described in detail with reference to the drawings, in which like reference numerals designate identical or corresponding elements in each of the several views. As used herein the term "distal" refers to that portion of the adapter assembly or surgical stapler, or component thereof, farther from the user, while the term "proximal" refers to that portion of the adapter assembly or surgical device, or component thereof, closer to the user. As used herein the term "user" will refer to a surgeon, a clinician, or other operating room personnel.

The surgical staplers of the present disclosures are configured to facilitate introduction and positioning of a stapling assembly of the surgical staplers into a body cavity of a patient through natural orifices or incisions around contours and curvatures of the anatomy within the patient. The introducer assemblies of the present disclosure also facilitate introduction and positioning of the stapling assembly of the surgical staplers within the patient.

Figure 2:
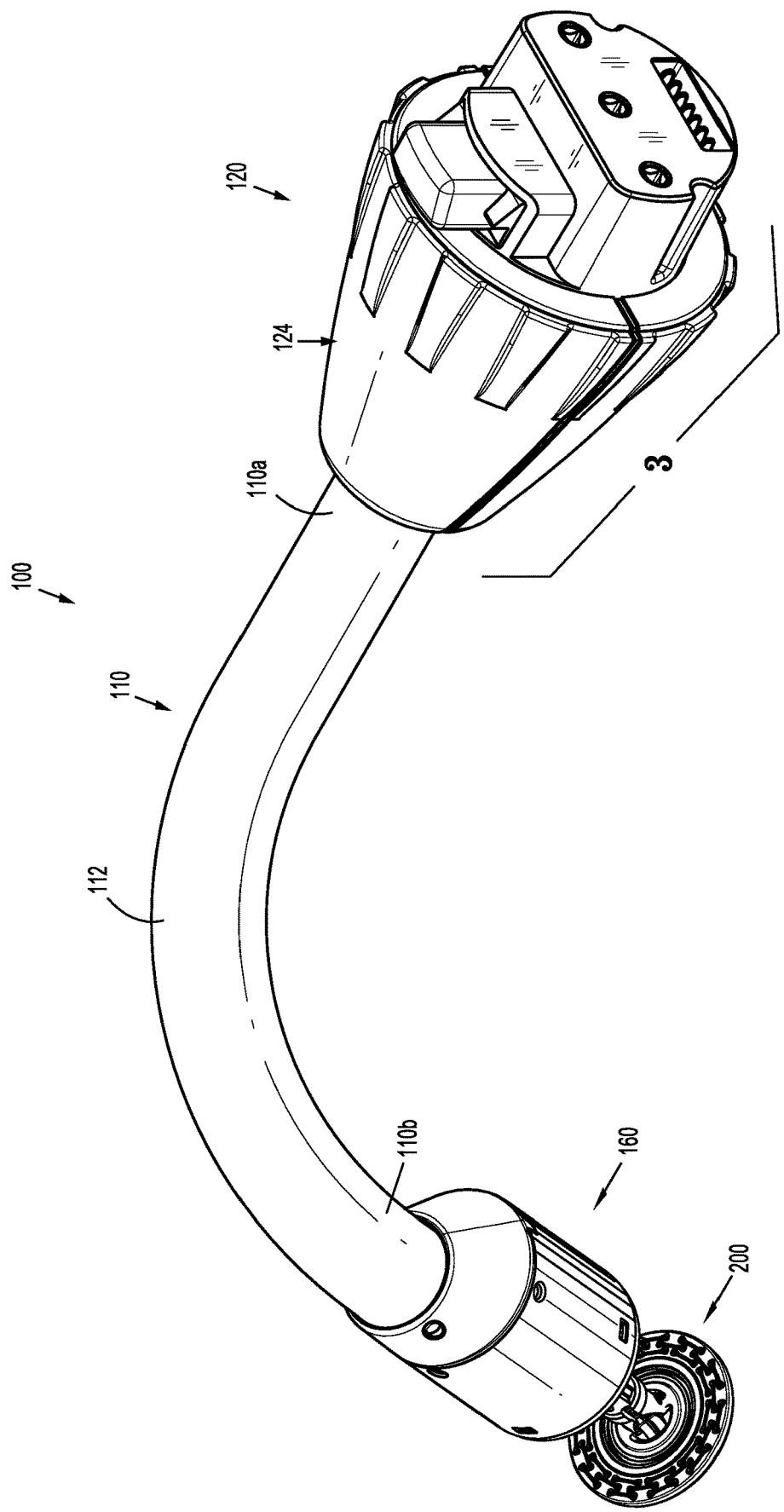
FIG. 2 is a side perspective view of the adapter assembly shown in FIG. 1.

With reference to FIGS. 1 and 2, an adapter assembly in accordance with an embodiment of the present disclosure, shown generally as adapter assembly 100, is configured for selective connection to a powered handheld electromechanical instrument, shown generally as handle assembly 20. Although shown as including the powered handle assembly 20, it is envisioned that the adapter assembly 100 of the present disclosure may be used with a manually actuated handle assembly or a robotically controlled surgical system (not shown).

As illustrated in FIG. 1, the handle assembly 20 is configured for selective connection with the adapter assembly 100, and, in turn, the adapter assembly 100 is configured for selective connection with an anvil assembly 200. Collectively, the adapter assembly 100, the handle assembly 20, and the anvil assembly 200, form a surgical stapling device 10. For a detailed description of the structure and function of an exemplary powered handle assembly, please refer to commonly owned U.S. Pat. No. 9,055,943 and U.S. Pat. App. Pub. No. 2016/0310134 ("the '943 publication"), the content of each of which is incorporated by reference herein in its entirety.

With continued reference to FIGS. 1 and 2, the adapter assembly 100 includes an elongate body 110, and a coupling assembly 120 supported on a proximal portion 110a of the elongate body 110 for securing the elongate body 110 to the handle assembly 20. The elongate body 110 includes a flexible sleeve 112 that may be formed from selectively-rigid memory metal, semi-flexible material, bellows, and/or from any suitable material. The elongate body 110 further includes a mounting member 114 (FIG. 3) secured within a proximal portion of the flexible sleeve 112. The mounting member 114 includes a flange 116 for engaging a handle member 124 of the coupling assembly 120 to secure the elongate body 110 of the adapter assembly 100 to the coupling assembly 120 of the adapter assembly 100. The elongate body 110 is configured to permit bending and/or flexion of the elongate body 110 along its length such that the loading unit 160 may be selectively moved relative to the handle assembly 20 (FIG. 1) to facilitate positioning of the loading unit 160 within a patient (not shown).

Figure 3:
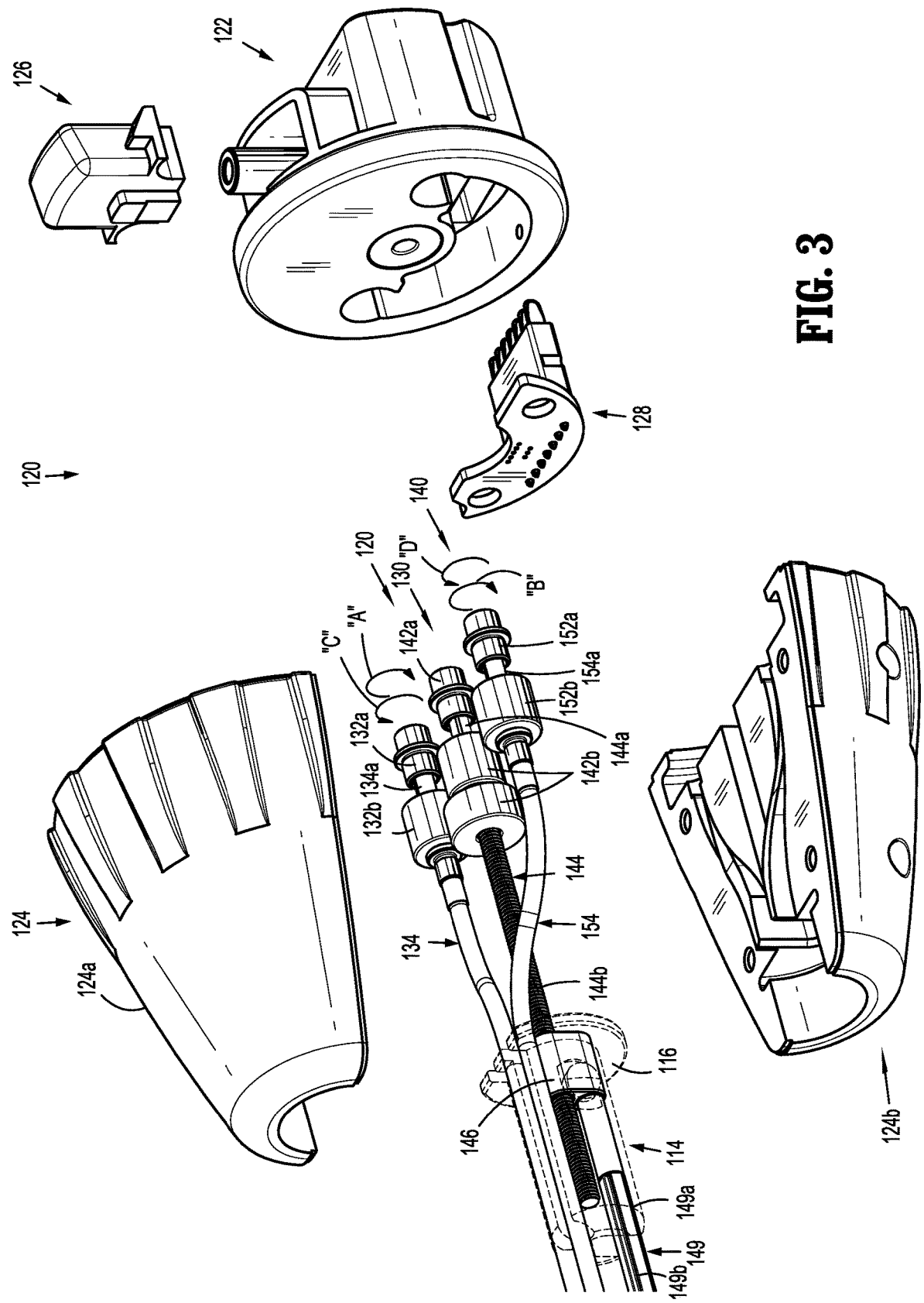
FIG. 3 is a side perspective view of a coupling assembly of the adapter assembly shown in FIG. 2, with parts separated.

With additional reference to FIG. 3, the coupling assembly 120 of the adapter assembly 100 is configured to releasably secure adapter assembly 100 to the handle assembly 20 (FIG. 1). As noted above, the handle assembly 20 (FIG. 1) includes a powered handle assembly 22. As will become apparent from the following disclosure, the handle assembly 20 may include any mechanism suitable for actuating first, second, and third drive assemblies 130, 140, 150. It is envisioned that each of the first, second, and third drive assemblies 130, 140, 150 may be actuated by the same drive member (not shown) of a handle assembly (not shown), or each of the first, second, and third drive assemblies 130, 140, 150 may be actuated by respective first, second, and third drive members (not shown) of the handle assembly 20.

With continued reference to FIG. 3, the coupling assembly 120 of the adapter assembly 100 includes a base member 122, a first handle half 124a and a second handle half 124b (collectively, handle member 124) mounted to the base member 122, a release button 126 operably secured to the base member 122, and an electric connector 128 disposed within the base member 122. The base member 122 is configured for releasable connection to the handle assembly 20. For a detailed description of the structure and function of an exemplary coupling assembly, please refer to commonly owned U.S. Pat. App. Pub. No. 2015/0157321, the content of which is incorporated by reference herein in its entirety, and the previously incorporated '943 publication.

The adapter assembly 100 further includes the first, second, and third drive assemblies 130, 140, 150, for performing first, second, and third functions. In embodiments, the first drive assembly 130 is configured to effect gross approximation of the anvil assembly 200 relative to the loading unit 160, e.g., course clamping, the second drive assembly 140 configured to effect fine approximation of the anvil assembly 200 relative to the loading unit 160, e.g., fine clamping, and the third drive assembly 150 is configured to effect firing of the loading unit, e.g., stapling.

Still referring to FIG. 3, the first, second, and third drive assemblies 130, 140, 150 include respective, first, second, and third connector member 132a, 142a, 152a configured for releasably connecting drive members (not shown) of the handle assembly 20 (FIG. 1) to respective first, second, and third drive shafts 134, 144, 154, of the respective first, second, and third drive assemblies 132, 142, 152. First and third bearing members 132b, 152b support respective first and third drive shafts 134, 154 of the first and third drive assemblies 132, 152, and a second bearing assembly 142b supports a drive screw 144 of the second drive assembly 140.

Figure 7:
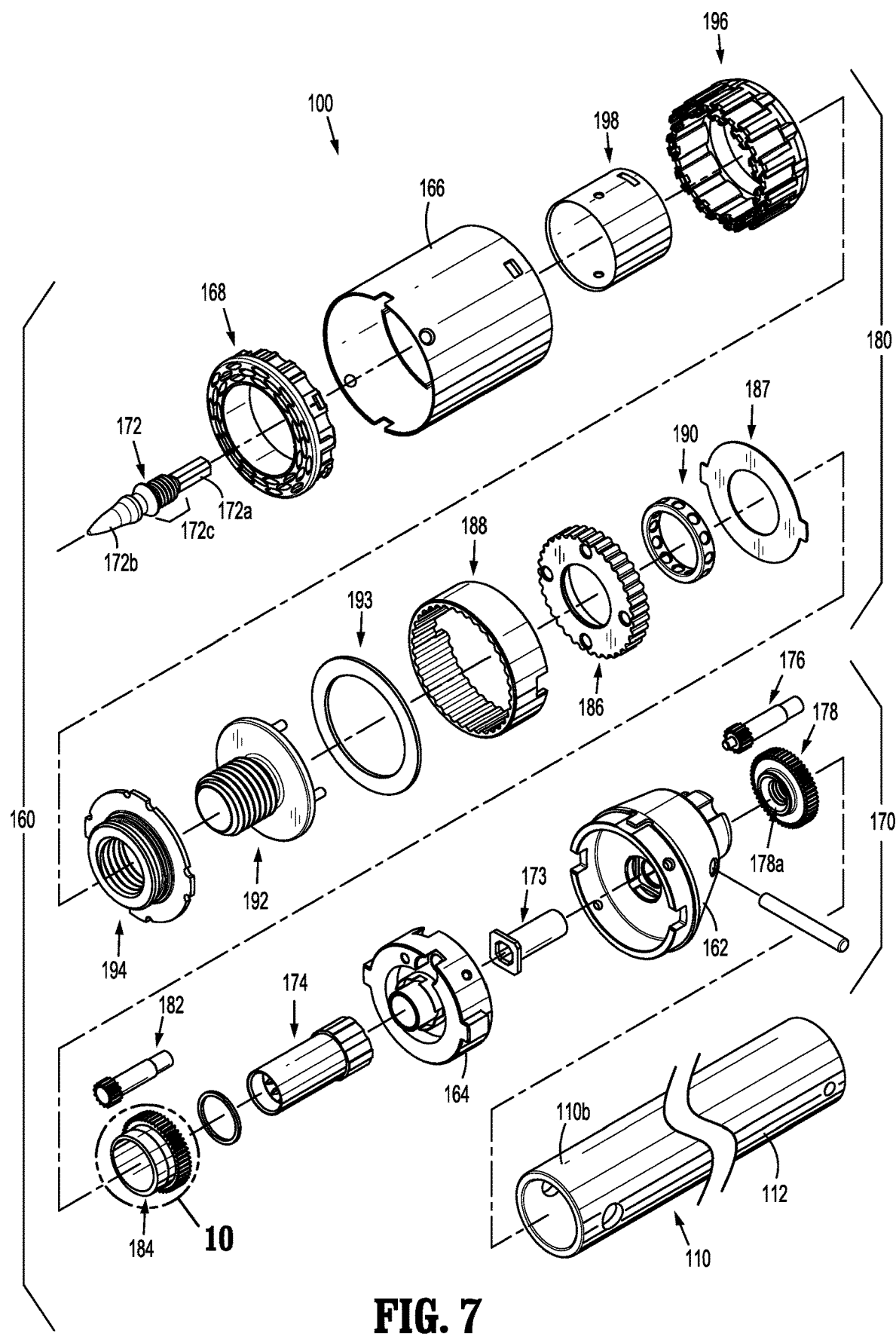
FIG. 7 is a side perspective view of the loading unit shown in FIG. 6, with parts separated.

Each of the first and third drive shafts 134, 154 of the first and third drive assemblies 130, 150, respectively, of the adapter assembly 100 extends the length of the elongate body 110 of the adapter assembly 100. More particularly, proximal portions 134a, 154a of the respective first and second drive shafts 134, 154 operably engage the respective first and second connector members 132a, 152a of the respective first and third drive assemblies 130, 150, and distal portions 134b, 154b (FIG. 17) of the respective first and third drive shafts 134, 154 support respective input gears 176, 182 (FIG. 17) of a respective approximation assembly 170 (FIG. 7) and a firing assembly 180 (FIG. 7).

During actuation of the first and third drive assemblies 130, 150, rotation of the first and third connector members 132a, 152a, respectively, about their longitudinal axis in a first direction, e.g., clockwise, as indicated by arrows "A" and "B", respectively, causes rotation of the respective first and third drive shafts 134, 154 in the same, first direction, about their respective longitudinal axis to effect first and third functions. Conversely, rotation of the first and third connector members 132a, 152a, respectively, about their longitudinal axis in a second direction, e.g., counter-clockwise, as indicated by arrows "C" and "D", respectively, causes rotation of the respective first and third drive shafts 134, 154 in the same, second direction, about their respective longitudinal axis to effect first and third functions. As described herein, the first and third drive assemblies 130, 150 operate to effect the fine clamping and firing functions, respectively, of the loading unit 160 of the adapter assembly 100. Although the loading unit 160 is shown, and will be described, as securely affixed to the elongate body 110, it is envisioned that the loading unit 160 may be at least partially releasable from the elongate body 110 to permit reuse of the adapter assembly 100.

In embodiments, and as shown, the first and third drive shafts 134, 154 of the first and third drive assemblies 130, 150, respectively, are formed as one-piece, e.g., integrally or monolithically formed, such that the entire first and second drive shafts 134, 154 rotate about their respective longitudinal axes. Alternatively, either or both of the drive shafts 134, 154 may include an outer sleeve (not shown) and a rotatable inner shaft (not shown).

With additional reference to FIG. 5, the second drive shaft 144 of the second drive assembly 140 of the adapter assembly 100 is in the form of a drive screw, and includes a proximal portion 144a that operably engages the second connector member 142a of the second drive assembly 140, and a threaded distal portion 144b. In embodiments, and as shown, the threaded distal portion 144b of the second drive shaft 144 is maintained almost entirely within the handle member 124 of the coupling assembly 120 of the adapter assembly 100. In this manner, the threaded distal portion 144b of the second drive shaft 114 may be rigid without interfering with the flexibility of the elongate body 110 of the adapter assembly 100. The threaded distal portion 144b of the second drive shaft 144 supports a nut member 146. More particularly, the nut member 146 defines first and second threaded throughbores 147a, 147b. The threaded portion 144b of the second drive shaft 144 is received through the throughbore 147a in a threaded manner.

In embodiments, and as shown, the second threaded throughbore 147b of the nut member 146 of the second drive assembly 140 of the adapter assembly 100 receives a threaded proximal portion 148a of a connector 148 of a push/pull member 149 of the second drive assembly 140. The threaded engagement between the connector 148 and the push/pull member 149 secures the push-pull member 149 to the nut member 146. Although shown including a threaded engagement, it is envisioned that the nut member 146 and connector 148 may be secured to one another in any suitable fashion, e.g., welding, adhesive, friction fit.

The push-pull member 149 of the second drive assembly 140 of the adapter assembly 100 includes an outer sleeve 149a, and an inner cable 149b slidably disposed within the outer sleeve 149a. The outer sleeve 149a of the push-pull member 149 may include a semi-rigid flexible sheath, or a coil spring, or any other flexible tubular member suitable for transferring an axial force in the distal direction, e.g., pushing force. The inner cable 149b of the push-pull member 149b may include a wire, a cord, or any other material suitable for transferring an axial force in a proximal direction, e.g., pulling force. In embodiments, the inner cable 149b is a stainless steel braided cable. The outer sleeve 149a may be a spring winding wrapped around the braided cable. Both the outer sleeve 149a and the inner cable 149b are flexible to accommodate the flexion of the elongate body 110 of the adapter assembly 100.

With continue reference to FIG. 5, during actuation of the second drive assembly 140, rotation of the second connector member 142a of the second drive assembly 140 about its longitudinal axis in a first direction, e.g., clockwise, as indicated by arrow "E", causes rotation of the second drive shaft 144 of the second drive assembly 140 about its longitudinal axis in the same, clockwise direction. As the second drive shaft 144 of the second drive assembly 140 rotates in the clockwise direction, threaded engagement between the nut member 146 and the threaded distal portion 144*b* of the second drive shaft 144 causes longitudinal movement of the nut member 146 relative to the second drive shaft 140 in a distal direction, e.g., advancement, as indicated by arrow "F".

Conversely, rotation of the second connector member 142*a* of the second drive assembly 140 about its longitudinal axis in a second direction, e.g., counter-clockwise, as indicated by arrow "G", through operation of the handle assembly 20 (FIG. 1) causes rotation of the second drive shaft 144 of the second drive assembly 140 about its longitudinal axis in the same, counter-clockwise direction. As the second drive shaft 144 of the second drive assembly 140 rotates in the counter-clockwise direction, threaded engagement between the nut member 146 and the threaded distal portion 144*b* of the second drive shaft 144 causes longitudinal movement of the nut member 146 relative to the second drive shaft 140 in a distal direction, e.g., advancement, as indicated by arrow "H".

Figure 6:
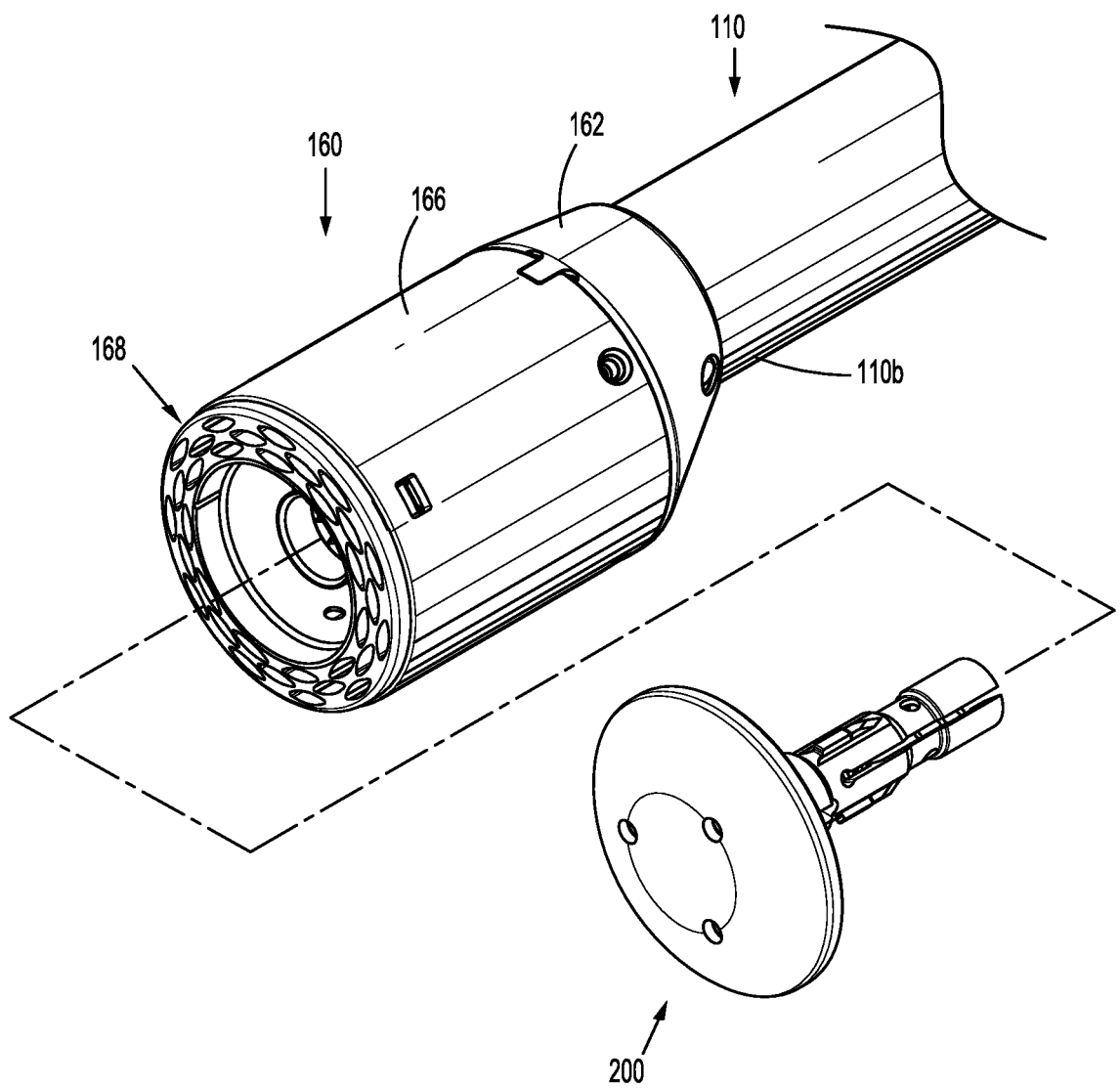
FIG. 6 is a perspective view of a loading unit of the adapter assembly and anvil assembly shown in FIG. 1.
Figure 8:
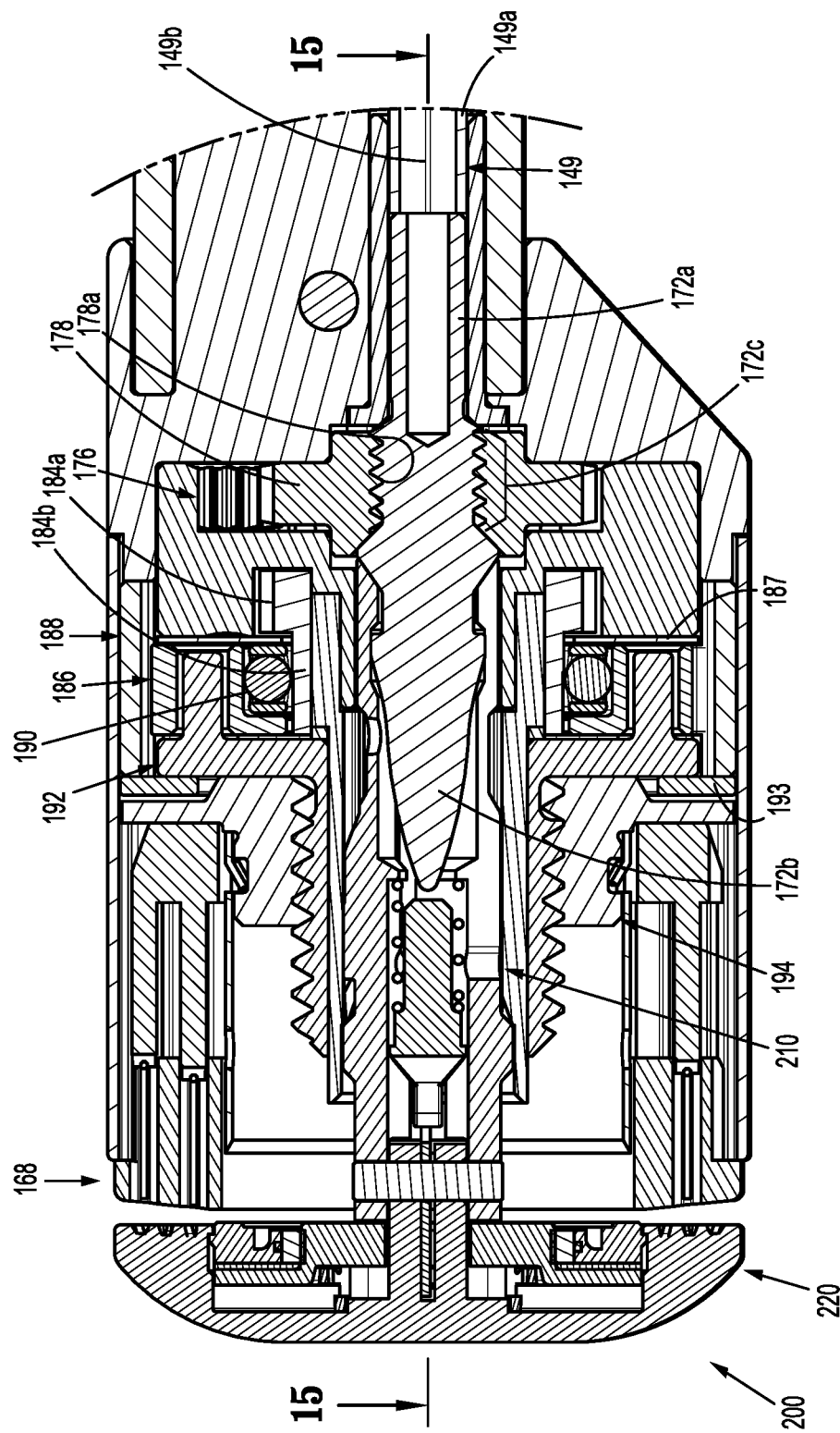
FIG. 8 is an enlarged view of the indicated area of detail in FIG. 4.
Figure 21:
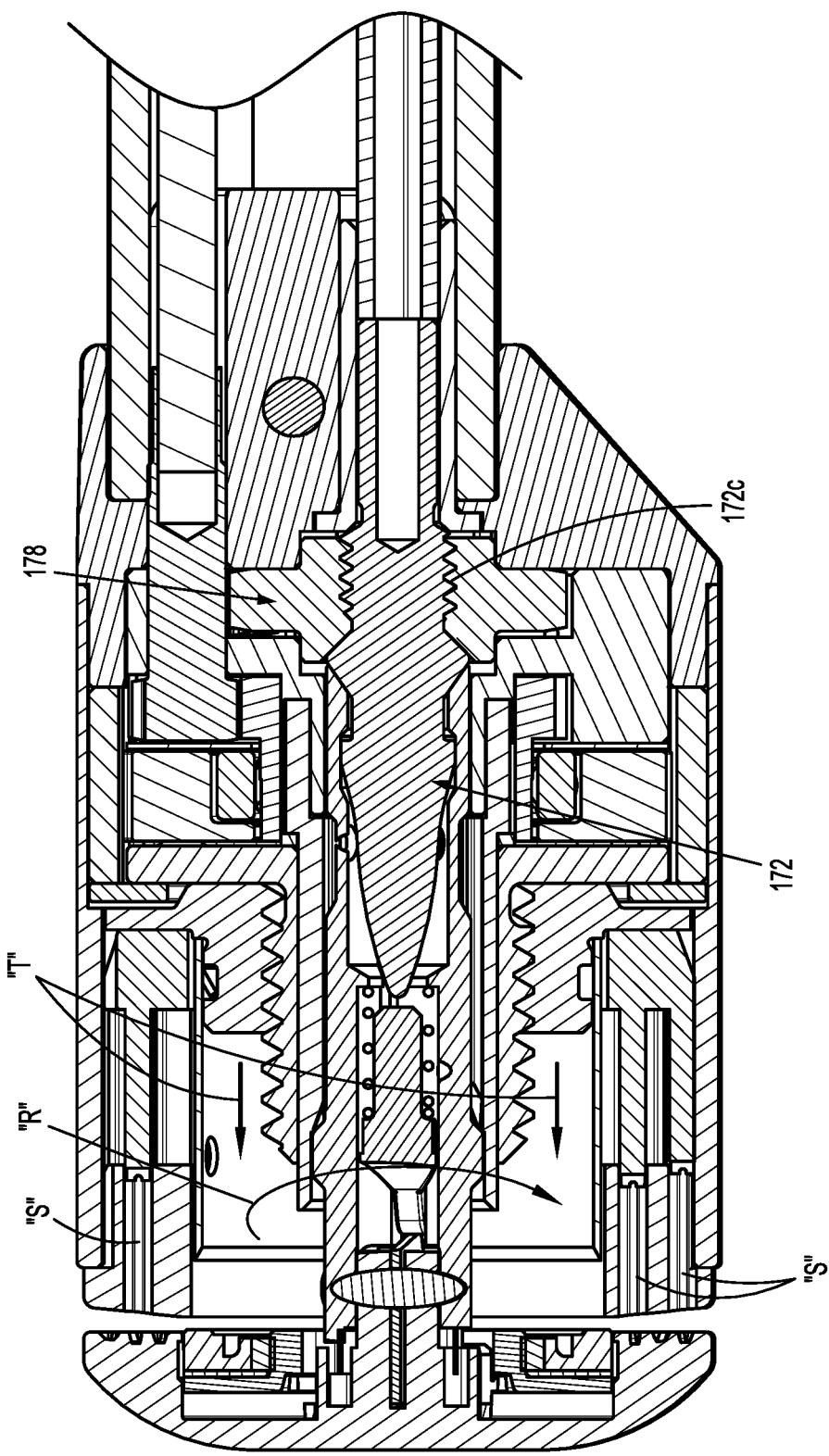
FIG. 21 is a side cross-sectional view taken along line 21-21 shown in FIG. 18.

With particular reference to FIGS. 6-8, the loading unit 160 of the adapter assembly 100 is supported on the distal portion 110*b* of the elongate body 110 of the adapter assembly 100. The compact design of the loading unit 160 facilitates introduction of the loading unit 160 into a body cavity (not shown) of a patient (not shown). As noted above, the loading unit 160 may be integrally formed with the elongate body 110, or may be releasably secured thereto to permit reuse of the adapter assembly 100. The loading unit 160 includes a main housing 162, a secondary housing 164 secured to the main housing 162, and a shell member 166 received about the main and secondary housings 162, 164. A staple cartridge 168 is supported on a distal portion of the shell member 166 and is configured to dispense a circular array of staples "S" (FIG. 21). The staple cartridge 168 may be separable from the shell member 166 to permit replacement of the staple cartridge 168 following a stapling procedure. In this manner, the adapter assembly 100 and/or the loading unit 160 may be reused.

An approximation assembly 170 is operably supported within the main and secondary housings 162, 164 of the loading unit 160, and is configured for gross and fine approximation of the anvil assembly 200 relative to the cartridge assembly 168 of the loading unit 160. More particularly, the approximation assembly 170 includes a trocar member 172 secured to the distal portion of the push/pull cable 149 (FIG. 8) of the second drive assembly 140 (FIG. 3), a trocar guide 173 for guiding the trocar member 172 during approximation of the anvil assembly 200 relative to the loading unit 160, and a spline tube 174 configured to secure the anvil assembly 200 to the trocar member 172 during approximation of the anvil assembly 200 relative to the loading unit 160 and during firing of the loading unit 160.

The trocar member 172 includes a proximal portion 172*a* configured for secured connection to the distal portion of the push/pull cable 149 of the second drive assembly 140. The proximal portion 172*a* of the trocar member 172 is bonded, welded, adhered, mechanically fastened, frictionally fit, or otherwise secured to the distal portion of the push/cable 149. A distal portion 172*b* of the trocar member 172 is configured to facilitate releasable connection with a center rod assembly 210 of the anvil assembly 200. The distal portion 172*b* of the trocar member 172 may further be configured to facilitate piercing of tissue during a stapling procedure. An intermediate portion 172*c* of the trocar member 172 is threaded to permit fine approximation of the anvil assembly 200 relative to the reload unit 160, as will be described in further detail below.

The approximation assembly 170 of the loading unit 160 further includes an input gear 176 rotatably supported within the main housing 162 of the loading unit 160 and an internally threaded gear 178 rotatably supported between the main housing 162 and the secondary housing 164, and in operable engagement with the input gear 176. The input gear 176 is fixedly secured to a distal portion 134*b* of the first drive shaft 134 of the first drive assembly 130, and is configured to rotate the internally threaded gear 178. As shown in FIG. 8, the distal portion of the push/pull cable 149 and the proximal portion 172*a* of the trocar member 170 are receivable through the threaded opening 178*a* of the internally threaded gear 178 such that the threaded intermediate portion 172*c* of the trocar member 172 engages the internally threaded gear 178 in a threaded manner.

As will be described in further detail below, when the push/pull cable 149 of the second drive assembly 140 is sufficiently retracted during gross approximation of the anvil assembly 200 relative to the loading unit 160 such that the threaded intermediate portion 172*c* of the trocar member 172 engages the internally threaded gear 178, rotation of the internally threaded gear 178 causes fine longitudinal movement of the trocar member 172. The pitch of the threads of the internally threaded gear 178 and the threaded intermediate portion 172*c* of the trocar member 172 and/or the rate at which the internally threaded gear 178 is rotated may be varied to adjust the fine movement of the anvil assembly 200 relative to the loading unit 160. In embodiments, it is envisioned that the internally threaded gear 178 may be replaced by one or more helical wedges, or other suitable fine approximation mechanisms.

By positioning the components of the approximation assembly 170 within the loading unit 160, all of the forces are contained in the distal end of the surgical stapling device 10 (FIG. 1).

One or more sensors (not shown) may be disposed with the loading unit 160 and/or the anvil assembly 200 to measure the compression forces applied to tissue received between a head assembly 220 of the anvil assembly 200 and the staple cartridge 168 of the loading unit 160.

The loading unit 160 further includes a firing assembly 180 operably supported within the shell member 166 of the loading unit 160. The firing assembly 180 is actuated by the third drive assembly 150 of the adapter assembly 100 and effects the stapling and cutting of tissue (not shown) received between the anvil assembly 200 and the staple cartridge 178 of the loading unit 160.

With particular reference to FIG. 7, the firing assembly 180 includes an input gear 182 (FIG. 7), and an eccentric spur gear 184 in operable engagement with the input gear 182. The eccentric spur gear 184 engages a cycloid gear 186 which is received within a ring gear 188. A bearing assembly 190 is received within the cycloid gear 186 between the cycloid gear 186 and the eccentric spur gear 184 to facilitate rotation of the cycloid gear 186 relative to the ring gear 188. A spacer 187 may be received about the eccentric spur gear 184. A spider screw 192 operably engages the cycloid gear 186, and a jack nut 194 operably engages the spider screw 192. A spacer washer 193 may be received between the spider screw 192 and the cycloid gear 186. A pusher assembly 196, including a circular knife 198, is secured to the jack nut 194.

Figure 9:
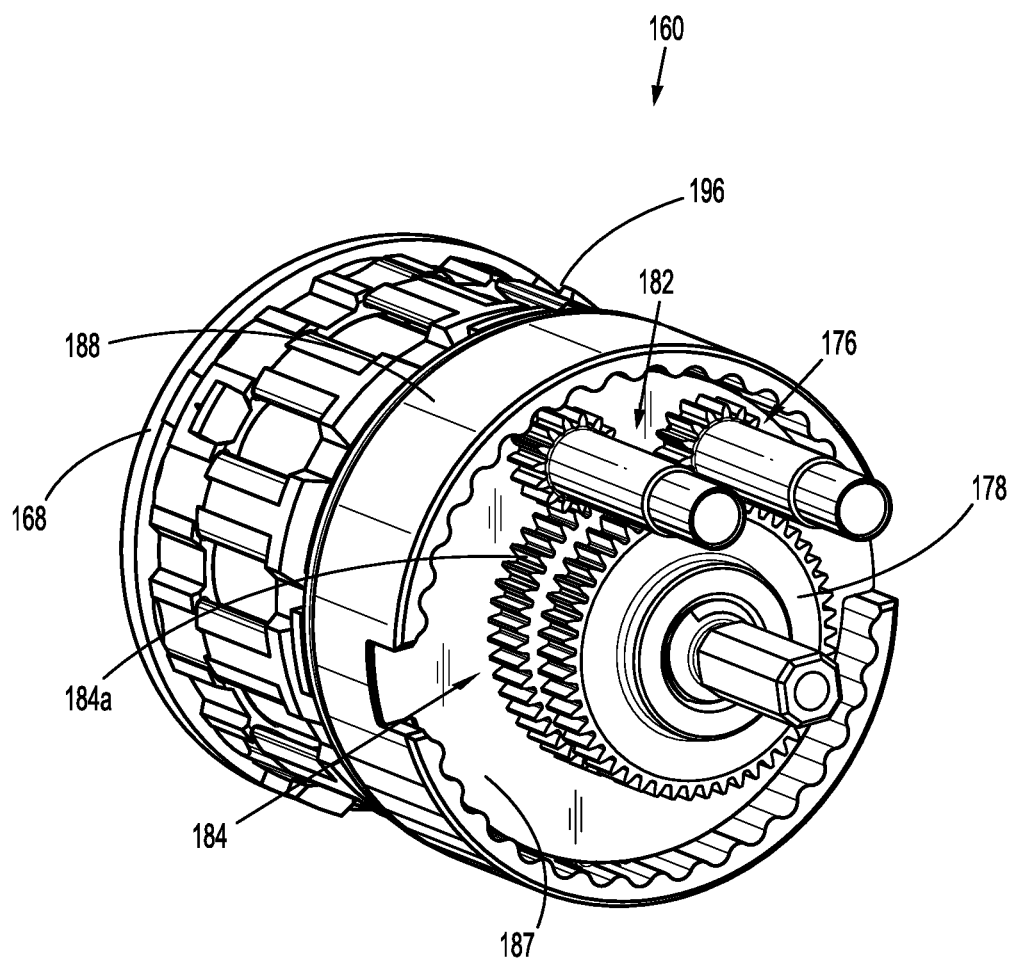
FIG. 9 is an end perspective view of the loading unit shown in FIG. 6, with a base member removed.

With reference now to FIG. 9, the input gear 182 of the firing assembly 180 of the loading unit 160 (FIG. 7) is secured to the distal portion 154*b* (FIG. 3) of the third drive shaft 154 (FIG. 3) of the third drive assembly 150 of the adapter assembly 100. The input gear 182 engages an externally geared proximal portion 184a of the eccentric spur gear 184. As shown, a diameter of the externally geared proximal portion 184a of the eccentric spur gear 184 is significantly larger than a diameter of the input gear 182. In this manner, the eccentric spur gear 184 rotates at a slower rate than the input gear 182, thereby operating to reduce the output speed. The direction of rotation of the eccentric spur gear 184 is opposite that of the input gear 182.

Figure 10:
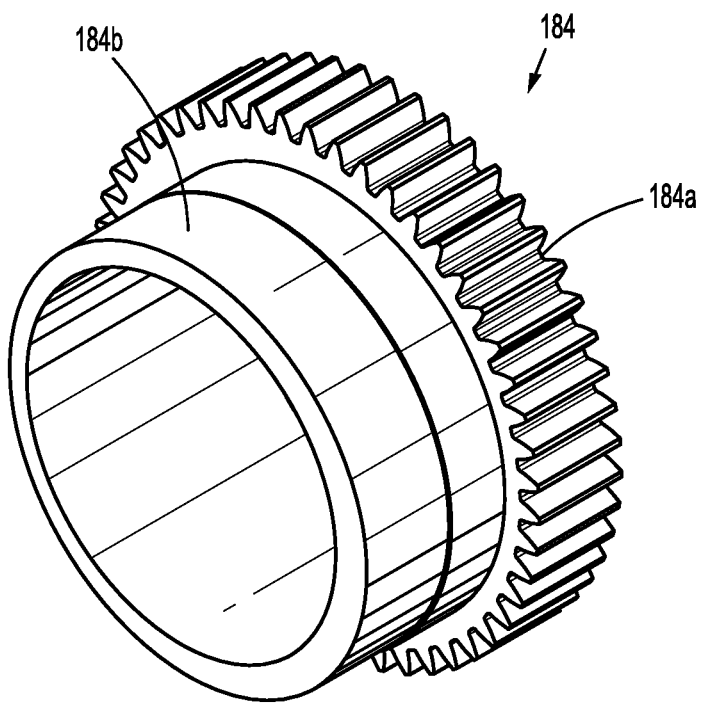
FIG. 10 is a perspective view of an eccentric gear of the loading unit shown in FIG. 6.
Figure 11:
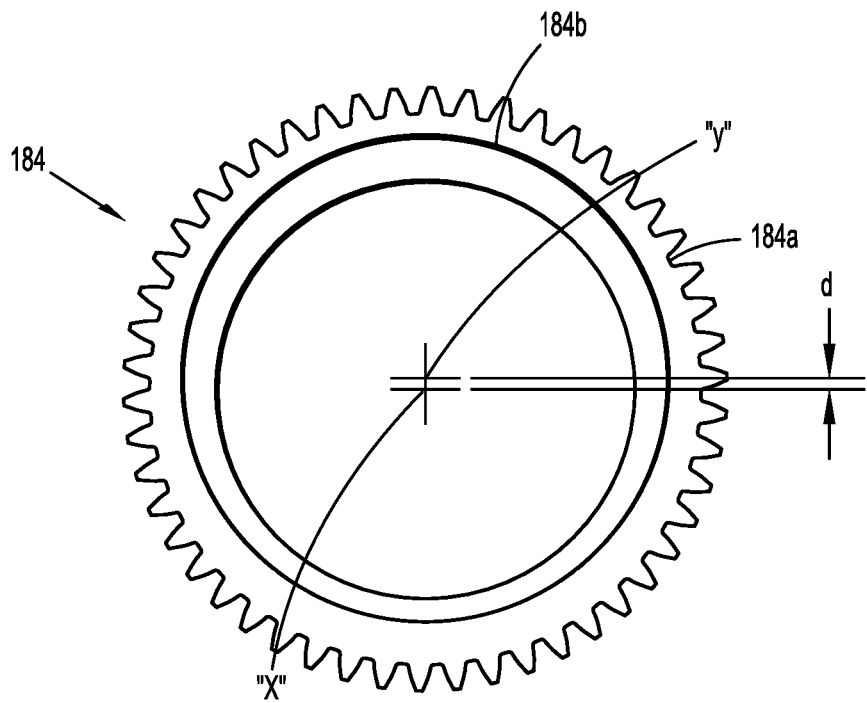
FIG. 11 is an end view of the eccentric gear shown in FIG. 10.

Turning now to FIGS. 10 and 11, the eccentric spur gear 184 of the firing assembly 180 of the loading unit 160 includes the externally geared proximal portion 184a and an eccentric distal portion 184b. The externally geared proximal portion 184a is configured to engage the input gear 182 of the firing assembly 180. With particular reference to FIG. 11, the eccentric distal portion 184b of the eccentric spur gear 184 defines a longitudinal axis "y" that is offset from a longitudinal axis "x" of the loading unit 160 by a distance "d". The length of distance "d" relates to a difference between the length of an outer diameter "$d_o$" (FIG. 13) of the cycloid gear 186 and a length of the inner diameter "di" (FIG. 13) of the ring gear 188.

Figure 12:
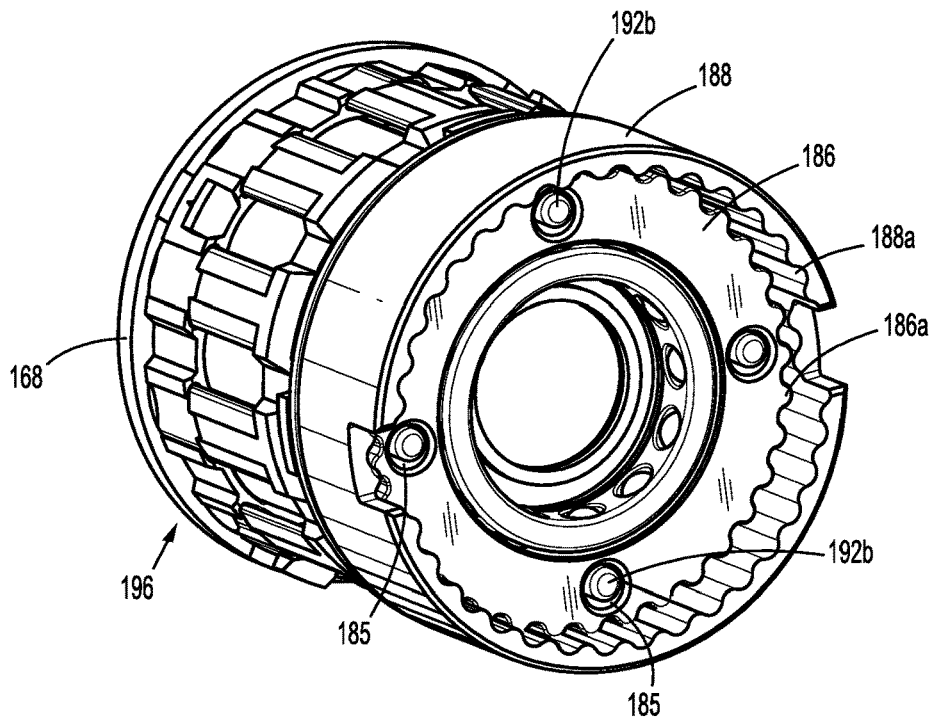
FIG. 12 is a perspective end view of the loading unit shown in FIG. 6 with a base member and the eccentric gear removed.
Figure 13:
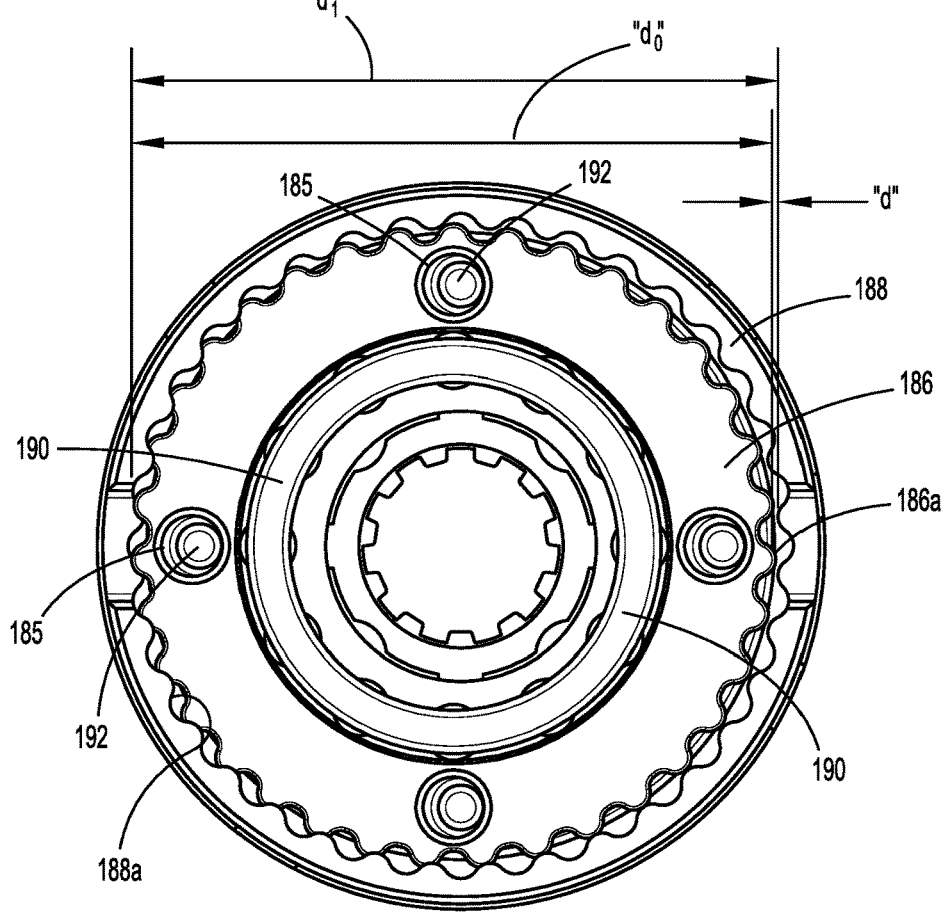
FIG. 13 is an end view of the loading unit shown in FIG. 6 with the base member and eccentric gear removed.

With reference now to FIGS. 12 and 13, the cycloid gear 186 is operably received within the ring gear 188, and with the eccentric spur gear 184, form a cycloid gear assembly. The outer diameter "$d_o$" of the cycloid gear 186 is the distance "d" less than the inner diameter "di" of the ring gear 188. As noted above, distance "d" is also the offset distance of the longitudinal axis "y" from the longitudinal axis "x". The bearing assembly 190 of the firing assembly 180 is received between the cycloid gear 186 and the eccentric portion 184b of the eccentric spur gear 184 (FIG. 8).

With particular reference to FIG. 13, because of the smaller outer diameter "$d_o$" of the cycloid gear 186 relative to the inner diameter "di" of the ring gear 188, and the corresponding offset of the eccentric portion 184b of the eccentric spur gear 186, only a portion of a toothed outer surface 186a of cycloid gear 186 engages a toothed inner surface 188a of ring gear 188. In this manner, rotation of the eccentric spur gear 184 (FIGS. 9-11) within the cycloid gear 186 cause the cycloid gear 186 to roll along the toothed inner surface 188a of the ring gear 188. The rolling of the cycloid gear 186 within the ring gear 188 reduces the rate of rotation of the cycloid gear 186 relative to the ring gear 188. The movement of the cycloid gear 186 relative to the ring gear 188 further operates to multiply the input torque from the second drive assembly 140 (FIG. 3). The direction of rotation of the cycloid gear 186 opposite that of the eccentric spur gear 188, or in the same direction as the input gear 182.

Although shown including a cycloid and ring gear assembly to multiply the input torque, it is envisioned that the cycloid gear 186 and ring gear 188 may be replaced by a planetary gear assembly (not shown). For a detailed description and function of an exemplary planetary gear system used in an adapter assembly, please refer to commonly owned U.S. Pat. App. Pub. No. 2016/0106406, the contents of which are incorporated by reference herein in their entirety.

With continued reference to FIGS. 12 and 13, the cycloid gear 186 includes a plurality of openings 185 configured to receive posts 192b that extend proximally from base 192a of the spider screw 192. The openings 185 have a diameter larger than a diameter of the posts 192a. This arrangement operates to accommodate the difference between the concentric rotation of the spider gear 192 relative to the longitudinal axis "x" and the non-concentric rotation of the cycloid gear 186 caused by the eccentric rotation of the eccentric distal portion 184b of the eccentric spur gear 184 during operation of the firing assembly 180. In this manner, as the cycloid gear 186 rolls about the inner surface 188b of the ring gear 188, the oversized nature of the openings 185 accommodate concentric rotation of the spider gear 192 about the longitudinal axis "x" while the cycloid gear 186 rotation is eccentric.

Figure 14:
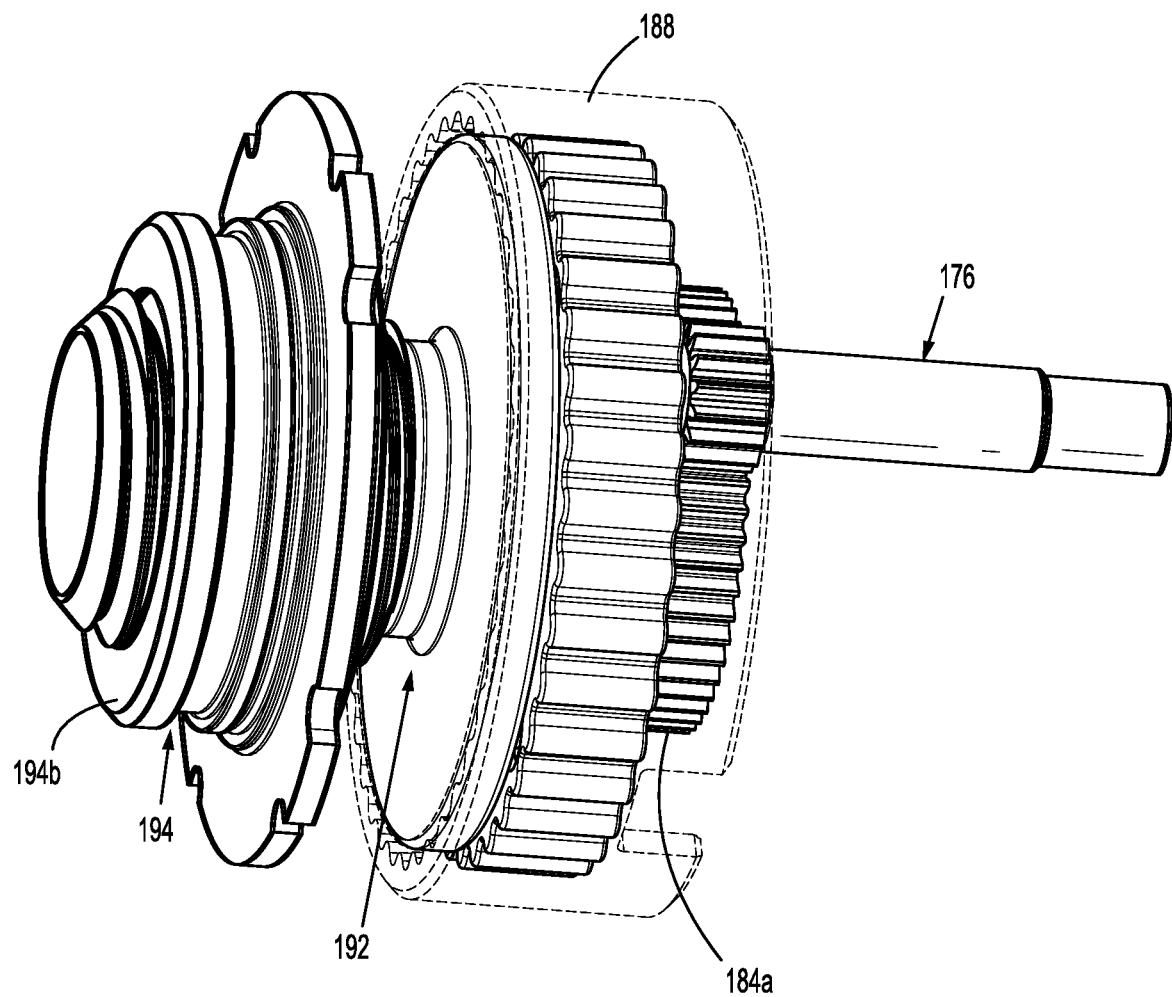
FIG. 14 is a side view of a stapling assembly of the loading unit shown in FIG. 6, without the pusher assembly.
Figure 15:
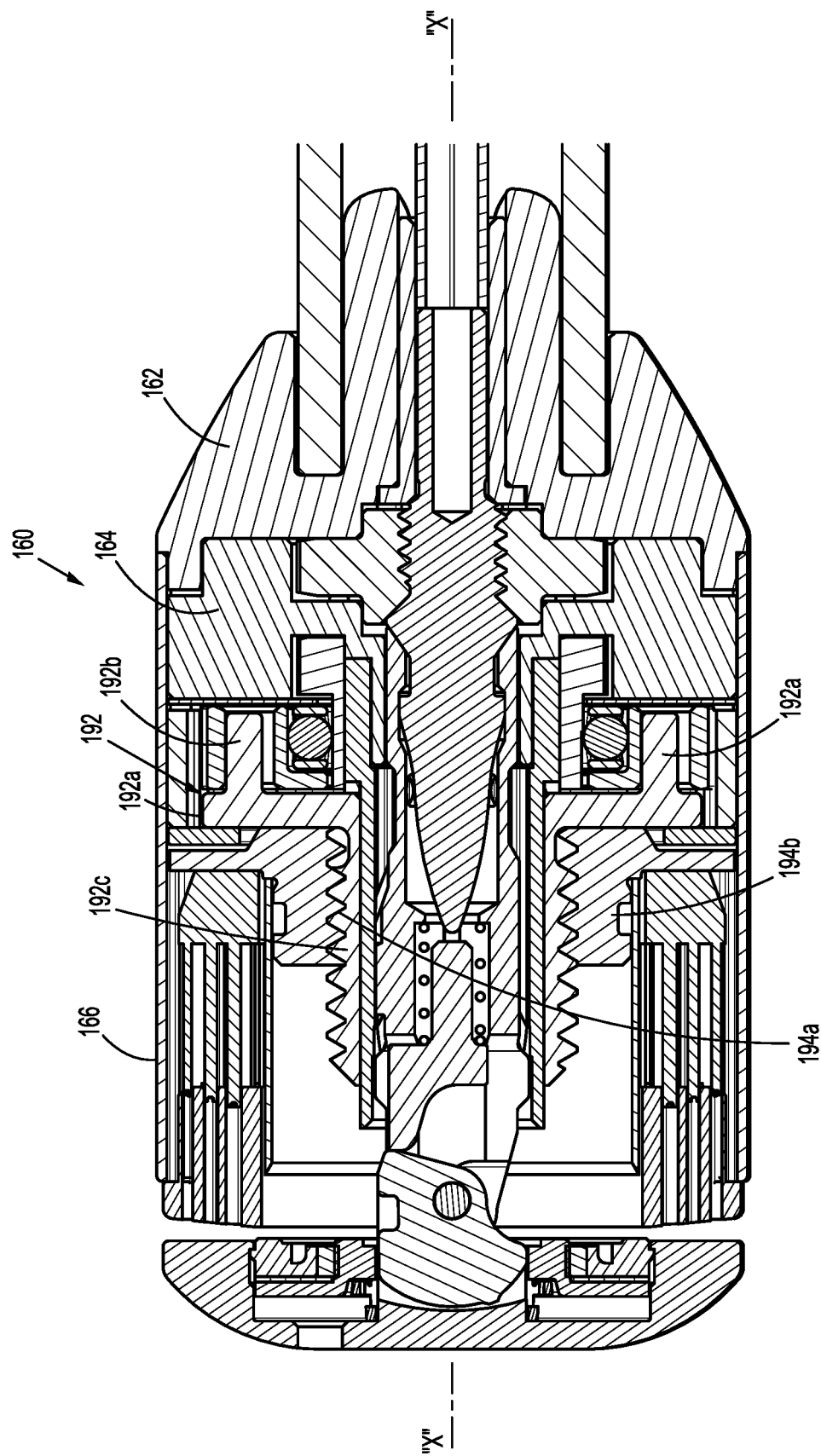
FIG. 15 is a cross-sectional view taken along line 15-15 shown in FIG. 8.

With reference to FIGS. 14 and 15, the spider gear 192 of the firing assembly 180 includes the base 192a, the plurality of proximally extending posts 192b, and a distally extending externally threaded flange 192c. Although shown including four (4) posts 192b (FIG. 13), it is envisioned that the spider gear 192 may include any number of posts 192b. The threaded flange 192c of the spider gear 192 supports the jack nut 194. More particularly, the jack nut 194 includes a threaded inner surface 194a that engages the threaded flange 192c of the spider gear 192 such that as the spider gear 192 rotates about the longitudinal axis "x", the jack nut 194 is moved along the longitudinal axis "x", e.g., advance or retracted.

The jack nut 194 of the firing assembly 180 includes a distally extending flange 194b that securely engages the pusher assembly 196 of the firing assembly 180. In this manner, as the jack nut 194 is moved in the distal direction, the pusher assembly 196 is also moved in the distal direction. Conversely, when the jack nut 194 is moved in the proximal direction, the pusher assembly 196 also moves in the proximal direction.

The pusher assembly 196 of the firing assembly 180 is substantially similar to the pusher assembly described in commonly owned U.S. Pat. No. 9,168,042 ("the '042 patent"), the content of which is incorporated herein by reference in its entirety.

Figure 16:
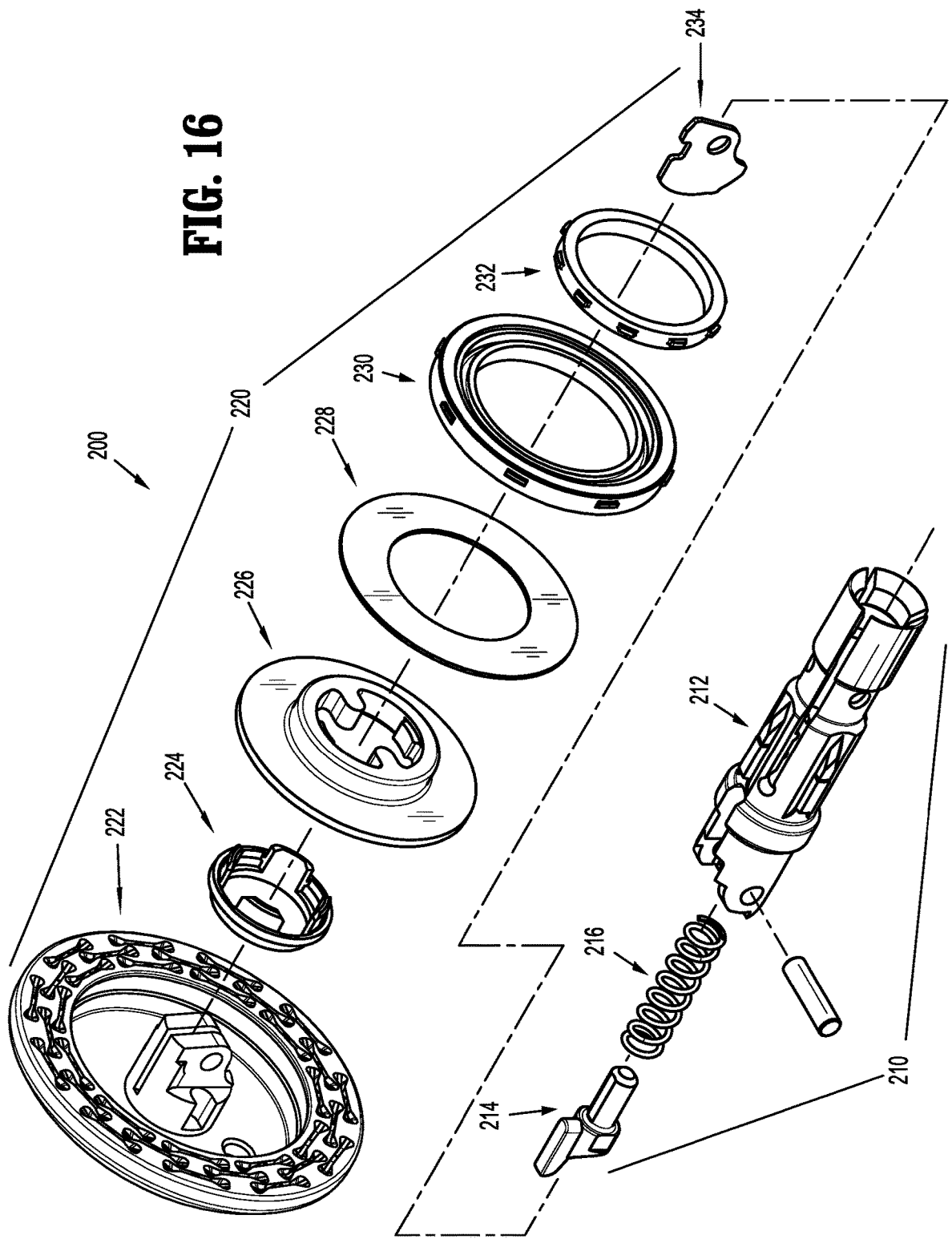
FIG. 16 is a side perspective view of the anvil assembly shown in FIG. 6, with parts separated.

Referring now to FIG. 16, the anvil assembly 200 of the surgical stapling device 10 includes a center rod assembly 210, and a head assembly 220 pivotally secured to the center rod assembly 210. Briefly, the center rod assembly 210 includes a center rod 212, a plunger member 214, and a spring member 216. The head assembly 220 includes a housing 222, a frangible ring 224, a backup member 226, a washer 228, a cut ring 230, a retaining sleeve 232, and a cam latch member 234. For a detailed description of the structure and function of an exemplary anvil assembly, please refer to commonly owned U.S. Pat. No. 9,554,802, the content of which is incorporated herein by reference in its entirety.

Figure 17:
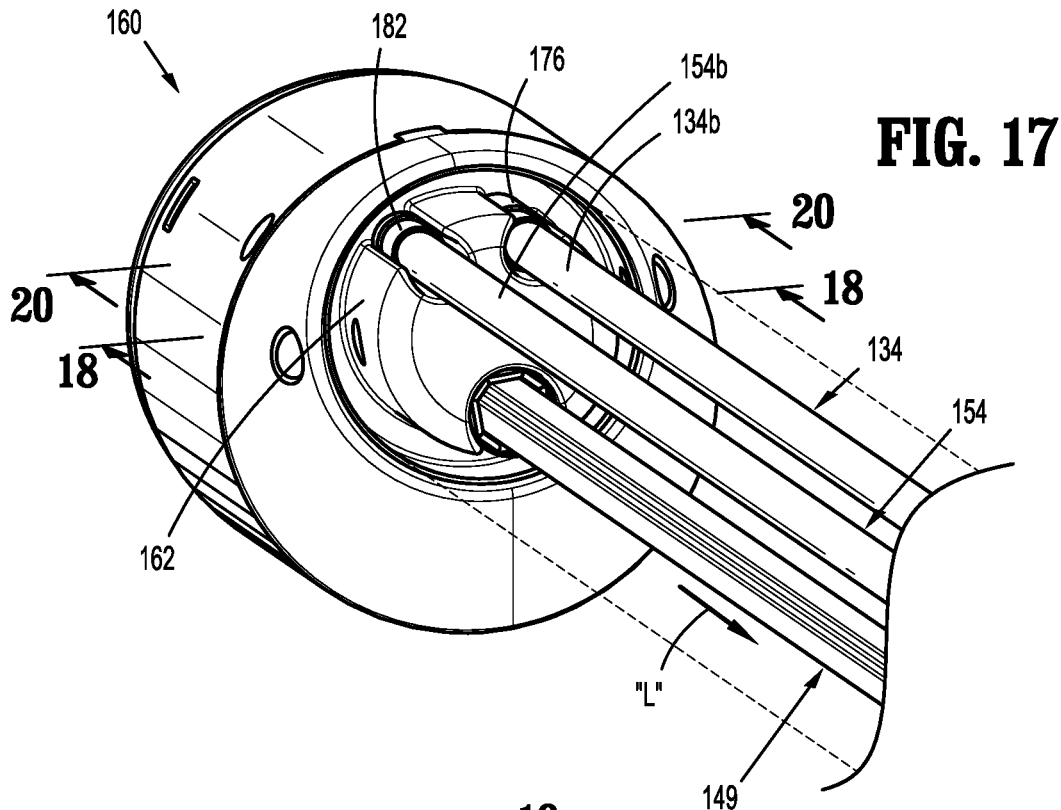
FIG. 17 is an end perspective view of the loading unit shown in FIG. 6 with an outer tube of the adapter assembly shown in FIG. 2 removed.

The operation of the loading unit 160 of the adapter assembly 100 will now be described with reference to FIGS. 17-21. Referring initially to FIG. 17, the first, second, and third drive assemblies 130, 140, 150 terminate in the loading unit 160. More particularly, the input gear 172 of the approximation assembly 170 (FIG. 7) is disposed on the distal portion 134b of the first drive shaft 134 of the first drive assembly 130 and is rotatably supported within the main housing 162 of the loading unit 160. The input gear 182 of the firing assembly 180 (FIG. 7) is disposed on the distal portion 154b of the third drive shaft 154 of the third drive assembly 150 and is rotatably supported within the main housing 162 of the loading unit 160. The distal portion of the push/pull cable 149, and the trocar member 172 secured thereto, are received through the main housing 162 of the loading unit 160.

As discussed in detail above, the approximation of the trocar member 172 is a two-step process effectuated by actuation of the second drive assembly 140 to complete gross approximation, followed by actuation of the first drive assembly 130 to complete fine approximation. Actuation of the second drive assembly 140 causes longitudinal movement of the push/pull cable 149 of the second drive assembly 140, and of the trocar member 172 of the approximation assembly 170. The second drive assembly 140 is configured for gross approximation of the push/pull cable 149. More particularly, actuation of the second drive assembly 140, as described above, causes retraction of the trocar member 172 and attached anvil assembly 200 into the spine tube 174 of the approximation assembly 170. Upon engagement of the intermediate portion 172c of the trocar member 172 with the internally threaded gear 178, the gross approximation of the anvil assembly 200 relative to the loading unit 160 is complete.

As discussed in detail above, actuation of the first drive assembly 130 of the surgical stapling device 10 effects fine approximation of the anvil assembly 200 of the surgical stapling device 10 relative to the loading unit 160 of the surgical stapling device 10. More particularly, actuation of the first drive assembly 130 causes rotation of the first drive shaft 134, which rotates the input gear 172 of the approximation assembly 170. Rotation of the input gear 172 in a first direction, e.g., clockwise, as indicated by arrow "M" in FIG. 19, rotates the internally threaded gear 178 of the approximation assembly in a second direction, e.g., counter-clockwise, as indicated by arrow "N" in FIG. 19.

Figure 18:
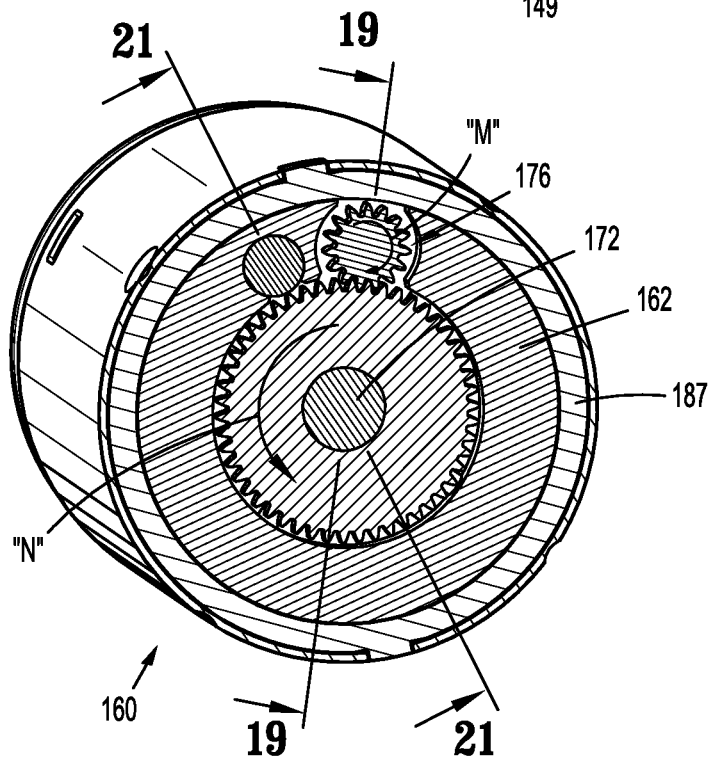
FIG. 18 is a cross-sectional view taken along line 18-18 shown in FIG. 17.

As the internally threaded gear 178 of the approximation assembly 170 is rotated in the first direction, the threaded engagement between the internally threaded gear 178 and the threaded intermediate portion 172c of the trocar guide 172 results in fine movement of the trocar member 172 in the proximal direction, as indicated by arrow "L" in FIG. 18, to permit the capture of tissue between the housing 212 of the head assembly 210 of the anvil assembly 200 and the cartridge assembly 168 of the loading unit 160. More particularly, fine approximation of the trocar member 172 enables a user to approximate the anvil assembly 200 relative to the loading unit 160 to compress tissue therebetween until an optimum compression is achieved. As noted above, the approximation assembly 170 is configured such that the forces contained within the distal end of the surgical stapling device 10 (FIG. 1).

One or more sensors (not shown) in the anvil assembly 200, loading unit 260, and/or along the first drive assembly 130 provide feedback to the handle assembly 20 to actuate the first drive assembly 130 to cause fine approximation of the anvil assembly 200 until the desired tissue compression is achieved.

As discussed in detail above, actuation of the third drive assembly 150 of the surgical stapling device 10 effects actuation of the firing assembly 180 (FIG. 7) of the loading unit 160. More particularly, actuation of the third drive assembly 150 causes rotation of the third drive shaft 154, which rotates the input gear 182 of the firing assembly 180. Rotation of the input gear 182 in a first direction, e.g., clockwise, as indicated by arrow "O" in FIG. 20, rotates the eccentric spur gear 184 of the firing assembly 180 in a second direction, e.g., counter-clockwise, as indicated by arrow "P" in FIG. 19, which, as described in detail, causes the rotation of the cycloid gear 190 in the first direction, e.g., clockwise, as indicated by arrow "Q" in FIG. 20. As also described in detail below, the rate of rotation of each of the input gear 182, the eccentric spur gear 184, and the cycloid gear 190 reduces progressively through the loading unit 160. Additionally, the eccentric spur gear 184, cycloid gear 186, and ring gear 188 operate together to multiply the input torque that is passed through the third drive assembly 150.

Figures 19, 20:
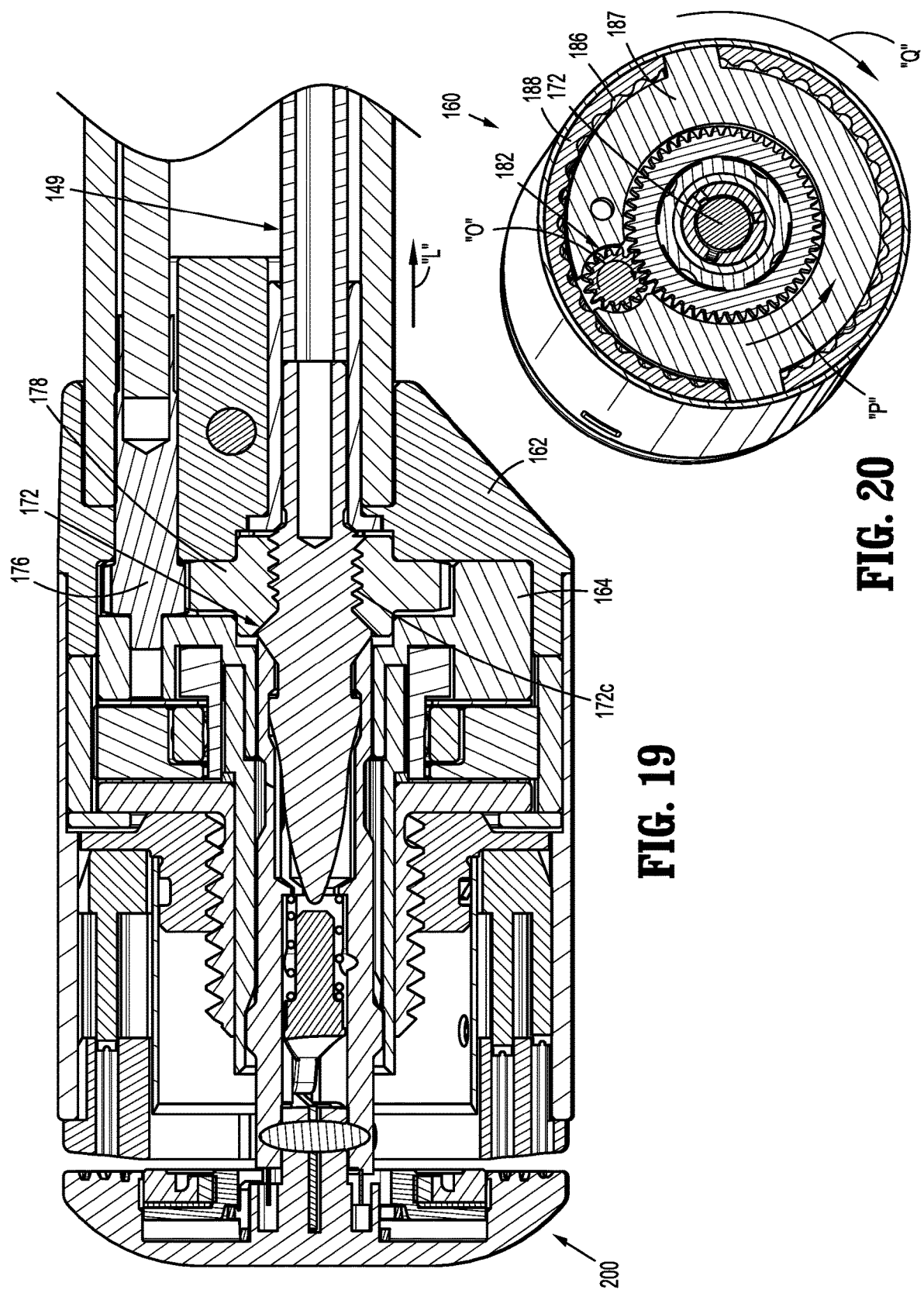
FIG. 19 is a side cross-sectional view taken along line 19-19 shown in FIG. 18.
FIG. 20 is a cross-sectional view taken along line 20-20 shown in FIG. 17.

With particular reference now to FIG. 21, as the cycloid gear 190 turns in a clockwise direction, as indicated by arrow "Q" in FIG. 20, the spider gear 192 turns in a clockwise direction, as indicated by arrow "R" in FIG. 21. Rotation of the spider gear 192 in the clockwise direction causes the jack nut 192 to move in a distal direction, as indicated by arrows "T", thereby moving the pusher assembly 196 to cause the ejection of staples "S" from the staple cartridge 168 and into the head assembly 220 of the anvil assembly 200.

In embodiments, and as shown, the knife 198 of the firing assembly 180 is secured to the pusher assembly 196. The advancement of the pusher assembly 196 causes advancement of the knife 198. In this manner, tissue (not shown) disposed between the head assembly 220 of the anvil assembly 200 and the staple cartridge 168 of the loading unit 100 and within a stapling surface of the housing 222 of the head assembly 220 is cut simultaneous with, or immediately following the stapling of tissue (not shown) between the stapling surface of the housing 222 and the staple cartridge 168.

Following the stapling of tissue (not shown), the third drive assembly 150 (FIG. 3) of the handle assembly 20 (FIG. 3) may be actuated in reverse to cause the retraction of the pusher assembly 196. Alternatively, the pusher assembly 196 may remain in a distal position (not shown), subsequent to the stapling of tissue. The first drive assembly 130 of the handle assembly 20 is actuated in reverse to cause an initial or fine movement of the trocar member 172 of the approximation assembly 170 in the distal direction. Once the threaded portion 172c of the trocar member 172 disengages from the internally threaded gear 178 of the approximation assembly 170, the second drive assembly 140 may be actuated in reverse to cause the gross movement of the trocar member 172 of the approximation assembly 170 to permit the release of the anvil assembly 200 from the trocar member 172 of the approximation assembly 170.

Turning now to FIGS. 22-28, an introducer for introducing a stapling end effector, e.g., loading unit 160 of surgical stapling device 10, according to an embodiment of the present disclosure is shown generally as introducer assembly 300. The introducer assembly 300 may be provided separate from the adapter assembly 100 described hereinabove, or as part of a kit. The introducer assembly 300 includes a sleeve body 310, a sleeve housing 320 disposed on a distal portion 310b of the sleeve body 310, and a pair of jaw members 330a, 330b secured to a distal portion 320b of the sleeve housing 320.

The sleeve body 310 is configured to be received about the elongate body 110 of adapter assembly 100 of the surgical stapling device 10, and the sleeve housing 320 is configured to be received about the loading unit 160 secured to the elongate body 110 of the surgical stapling device 10. The sleeve body 310 may be formed from an elastic material that permits flexion of the elongate body 110 of the adapter assembly. The elasticity of the sleeve body 310 may further permit receipt of the loading unit 160 therethrough. The sleeve housing 320 may be formed of the same flexible material as the sleeve body 310, or may instead be formed of a different material. The sleeve housing 320 may be formed a more rigid material than the sleeve body 310.

With particular reference now to FIGS. 24-26, the first and second jaw members 330a, 330b collectively form a substantially conical body portion 330 when the first and second jaw members 330a, 330b are in a closed condition (FIG. 22), and define an opening 331 when the first and second jaw members 330a, 330b are in a closed condition. Each of the first and second jaw members 330a, 330b is pivotally secured to a distal portion 320b of the sleeve housing 320. Each of the first and second jaw members 330a, 330b may be secured to the sleeve housing 320 with a living hinge, pivot pins (not shown), or in any other suitable manner. In embodiments, the first and second jaw members 330a, 330b are biased to the open condition. Alternatively, the first and second jaw members 330a, 330b may be permitted to pivot freely with respect to the sleeve housing 320 of the introducer assembly 300.

Each of the first and second jaw members 330a, 330b of the introducer assembly 300 includes a plurality of interlocking teeth 332a, 332b, respectively. At least two teeth of each of the plurality of interlocking teeth 332a, 332b of the respective first and second jaw members 330a, 330b define a transvers opening 331a, 331b, respectively, for receiving a suture 340. More particularly, with reference to FIG. 26, the suture 440 extends from external a proximal portion 310a of the sleeve body 310 distally through the sleeve body 310 and the sleeve housing 320, and through the openings in each of the interlocking teeth 332a, 332b, of the pair of jaw members 330a, 330b, respectively, when the pair of jaw members 330a, 330b is in the closed position. Receipt of the suture 340 through the openings 331 in the first and second jaw members 330a, 330b secures the first and second jaw members 330a, 330b in the closed condition.

With continued reference to FIG. 26, the suture 440 extends back through the sleeve housing 320 and the sleeve body 310, and extends out of the proximal portion 310a of the sleeve body 310. In this manner, first and second portions 340a, 340b of the suture 340 are received external of the sleeve body 310. Alternatively, either or both of the sleeve body 310 and sleeve housing 320 may define longitudinal channels (not shown) for receiving the suture 440 therethrough.

Referring now to FIG. 27, the introducer assembly 300 is shown received about the loading unit 160 and the distal portion 110b of the elongate body 110 of the adapter assembly 100. The pair of jaw members 330a, 330b of the introducer assembly 300 is secured in the closed condition by suture 340 (FIG. 25). In this closed condition, the introducer assembly 300 facilitates insertion of the loading unit 160 into a body cavity (not shown) of a patient (not shown). The flexible nature of the sleeve body 310 accommodates the receipt of the loading unit 160 along tortuous paths, e.g., through sections of an intestine.

Turning now to FIG. 28, when the loading unit 160 of the adapter assembly 100 is positioned in a desired location within the patient, the suture 340 is withdrawn from the openings 331a, 331b of the first and second jaw members 330a, 330b, respectively, by pulling on either of the first or second portion 340a, 340b of the suture 340. Once the suture 340 is withdrawn from the openings 331a, 331b of the first and second jaw members 330a, 330b, the first and second jaw members 330a, 330b are free to move to the open condition. As noted above, in embodiments, the first and second jaw members 330a, 330b are biased to the open condition. Alternatively, the first and second jaw member 330a, 330b may move to the open condition as the introducer is retracted relative to the loading unit 160 of the adapter assembly 100.

As shown in FIG. 28, whether biased opened or moved to the open condition through retraction of the introducer assembly 300 relative to the loading unit 160, as indicated by arrow "T", once the first and second jaw members 330a, 330b are in the open condition, the introducer assembly 300 may be removed from about the loading unit 160 and the distal portion 110b of the elongate body 110 of the adapter assembly 100. Once the introducer assembly 300 is retracted from about the loading unit 160, the surgical stapling device 10 may be used in a conventional manner, as described above.

With reference now to FIGS. 29-31, an introducer according to another embodiment of the present disclosure is shown generally as introducer 400. The introducer 400 is substantially similar to introducer assembly 300 described hereinabove, and will only be described in detail as relates to the differences therebetween.

The introducer assembly 400 includes a sleeve body 410, a sleeve housing 420 disposed on a distal portion 410b of the sleeve body 410, and first and second jaw members 430a, 430b secured to a distal portion 420b of the sleeve housing 420.

The first and second jaw members 430a, 430b collectively form a substantially conical body portion 430 when the first and second jaw members 430a, 430b are in a closed condition (FIG. 29), and define an opening 431 when the first and second jaw members 430a, 430b are in a closed condition. Each of the first and second jaw members 430a, 430b includes a plurality of tabs 432a, 432b, respectively, that each define an opening 431a, 431b. The tabs 432a, 432b of the respective first and second jaw members 430a, 430b overlap when the first and second jaw members 430a, 430b are in the closed condition. In this manner, a suture 440 is receivable through the openings 431a, 431b of the respective tabs 432a, 432b to secure the first and second jaw members 430a, 430b in the closed condition. Withdrawal of the suture 440 from within the openings 431a, 431b of the respective tabs 432a, 432b of the respective first and second jaw members 430a, 430b permits movement of the first and second jaw members to the open condition (not shown).

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An introducer assembly for facilitating introduction of a stapling assembly into a body cavity of a patient, the introducer assembly comprising:

a sleeve body having proximal and distal ends;

a sleeve housing disposed on the distal end of the sleeve body, the sleeve housing including proximal and distal portions; and first and second jaw members secured to the distal portion of the sleeve housing and moveable between an open condition and a closed condition, wherein each of the first and second jaw members includes a plurality of openings configured to receive a suture when the first and second jaw members are in the closed condition to maintain the first and second jaws in the closed condition, wherein each of the first and second jaw members includes a plurality of interlocking teeth, and wherein each tooth of the plurality of interlocking teeth defines an opening of the plurality of openings.

2. The introducer assembly of claim 1, wherein the first and second jaw members are pivotally secured to the distal end of the sleeve housing.

3. The introducer assembly of claim 1, wherein the first and second jaw members are pivotally secured to the distal end of the sleeve housing by a living hinge.

4. The introducer assembly of claim 1, wherein when the first and second jaw members are in the closed position, the first and second jaw members form a conical member.

5. The introducer assembly of claim 1, wherein the housing sleeve is configured to receive a stapling assembly of a circular stapling instrument.

6. The introducer assembly of claim 1, wherein the sleeve body is configured to receive a sleeve of a circular stapling instrument.

7. The introducer assembly of claim 1, wherein the first and second jaw members are biased to the open condition.

8. A kit comprising:
- an adapter assembly including a loading unit disposed on a distal end thereof, the loading unit including a firing assembly;
and
- an introducer member according to claim 1.

9. The kit of claim 8, further including a handle.

10. The kit of claim 9, further including an anvil assembly.

11. The kit of claim 8, wherein the sleeve housing of the introducer member is configured to receive the loading unit of the adapter assembly.

\* \* \* \* \*